US010975365B2

United States Patent
Kelman et al.

(10) Patent No.: US 10,975,365 B2
(45) Date of Patent: Apr. 13, 2021

(54) DI-ENZYMATIC CHIMERIC ENDOLYSIN

(71) Applicant: Government of the United States of America, as represented by the Secretary of Commerce, Gaithersburg, MD (US)

(72) Inventors: Zvi Kelman, Gaithersburg, MD (US); Daniel Craig Nelson, Rockville, MD (US); Xiaoran Shang, Ellicott City, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 0 days.

(21) Appl. No.: 16/670,194

(22) Filed: Oct. 31, 2019

(65) Prior Publication Data
US 2020/0140837 A1    May 7, 2020

Related U.S. Application Data

(60) Provisional application No. 62/755,869, filed on Nov. 5, 2018.

(51) Int. Cl.
| | | |
|---|---|---|
| *C12N 1/06* | (2006.01) | |
| *C12N 15/62* | (2006.01) | |
| *C12N 9/24* | (2006.01) | |
| *C12N 9/50* | (2006.01) | |

(52) U.S. Cl.
CPC ............. *C12N 9/2402* (2013.01); *C12N 1/06* (2013.01); *C12N 9/50* (2013.01)

(58) Field of Classification Search
CPC .......... C12N 1/06; C12N 9/2402; C12N 9/50; C12N 15/62
See application file for complete search history.

(56) References Cited

U.S. PATENT DOCUMENTS

| | | | |
|---|---|---|---|
| 7,582,729 B2 | 9/2009 | Fischetti et al. | |
| 7,838,255 B2 | 11/2010 | Fischetti et al. | |

OTHER PUBLICATIONS

Nelson, D., et al., "PlyC: A multimeric bacteriophage lysin", PNAS, 2006, p. 10765-10770, vol. 103 No. 28.
McGowan, S., et al., "X-ray crystal structure of the streptococcal specific phage lysin PlyC", PNAS, 2012, p. 12752-12757, vol. 109 No. 31.

*Primary Examiner* — Tekchand Saidha
(74) *Attorney, Agent, or Firm* — Office of Chief Counsel for National Institute of Standards and Technology

(57) ABSTRACT

A di-enzymatic chimeric endolysin includes a primary enzymatic active domain including a primary protein sequence and that cleaves a glycosidic, peptide, or amide bond; a secondary enzymatic active domain disposed at a C-terminus end of the di-enzymatic chimeric endolysin and including a secondary protein sequence that, in combination with the primary enzymatic active domain, synergistically cleaves glycosidic, peptide, or amide bonds in a peptidoglycan; a cell wall binding domain including a recognition sequence that is sequentially interposed between the primary protein sequence and the secondary protein sequence and that binds to a cell wall; and a tertiary structure such that the primary enzymatic active domain faces and opposes the secondary enzymatic active domain in the di-enzymatic chimeric endolysin for synergistic cleavage of the peptidoglycan.

20 Claims, 16 Drawing Sheets

Specification includes a Sequence Listing.

| Strain | Serotype | MIC (µg/ml) of: | | | | | | |
|---|---|---|---|---|---|---|---|---|
| | | Penicillin | Levofloxacin | Cpl-1 | ClyX-1 | GyH_Cpl-1 CBD | Cpl-1 CBD_CHAP | GyH_Cpl-1 CBD & Cpl-1 CBD_CHAP[a] | ClyX-3 |
| D39 | 2 | 0.06 | 0.5 | 16 | 0.13 | 32 | 16 | 16 | 4 |
| TIGR4 | 4 | 0.06 | 0.5 | 16 | 0.13 | 32 | 16 | 16 | 2 |
| DCC1335 | 9V (Sp9-3) | 4 | 2 | 32 | 0.5 | 128 | 16 | 32 | 16 |
| DCC1490 | 14 | 0.03 | 1 | 32 | 0.5 | 32 | 32 | 32 | 8 |
| DCC1476 | 15 | 0.5 | 2 | 32 | 0.5 | 64 | 32 | 32 | 16 |
| DCC1355 | 19 | 0.06 | 0.5 | 16 | 0.25 | 32 | 16 | 16 | 8 |
| DCC1420 | 23F (Sp23-1) | 2 | 2 | 32 | 0.5 | 64 | 16 | 32 | 8 |
| R6 | capsule free | 0.06 | 0.5 | 16 | 0.13 | 32 | 16 | 16 | 2 |

Figure 15

| Species | Strain | MIC (μg/ml) of: | | |
|---|---|---|---|---|
| | | PlySs2 | ClyX-2 | ClyX-4 |
| S. pyogenes (GAS) | D471 | 128 | 2 | 32 |
| | MGAS315 | 128 | 2 | 32 |
| | A486 | 128 | 2 | 32 |
| S. agalactiae (GBS) | A909 | 128 | 32 | 64 |
| | A349 | 256 | 32 | 128 |
| S. equi (GCS) | 9528 | >512 | 4 | 256 |
| GES | K131 | >512 | 64 | 256 |
| S. mutans | 10449 | >512 | 128 | 256 |
| | 25175 | >512 | 128 | 256 |
| S. uberis | BAA-854 | >512 | 64 | 256 |
| | 700407 | >512 | 64 | 256 |
| E. faecalis | JH2-2 | 512 | 64 | 256 |
| | EF-17 | 512 | 64 | 256 |
| S. suis | 730082 | 256 | >512 | 64 |
| S. aureus | NRS395 | 32 | >512 | >512 |

Figure 16

SEQUENCE LISTING

<160> NUMBER OF SEQ ID NOS: 22

<210> SEQ ID NO 1
<211> LENGTH: 205

<212> TYPE: PRT
<213> ORGANISM: Bacteriophage

<400> SEQUENCE: 1

Met Ser Lys Lys Tyr Thr Gln Gln Tyr Glu Lys Tyr Leu Ala Gln
1               5                   10                  15

Pro Ala Asn Asn Thr Phe Gly Leu Ser Pro Gln Val Ala Asp Trp
                20                  25                  30

Phe Met Gly Gln Ala Gly Ala Arg Pro Val Ile Asn Ser Tyr Gly Val
                35                  40                  45

Asn Ala Ser Asn Leu Val Ser Thr Tyr Ile Pro Lys Met Gln Glu Tyr
                50                  55                  60

Gly Val Ser Tyr Thr Leu Phe Leu Met Tyr Thr Val Phe Glu Gly Gly
65                  70                  75                  80

Gly Ala Gly Asn Trp Ile Asn His Tyr Met Tyr Asp Thr Gly Ser Asn
                85                  90                  95

Gly Leu Glu Cys Leu Glu His Asp Leu Gln Tyr Ile His Gly Val Trp
                100                 105                 110

Glu Thr Tyr Phe Pro Pro Ala Leu Ser Ala Pro Glu Cys Tyr Pro Ala
                115                 120                 125

Thr Glu Asp Asn Ala Gly Ala Leu Asp Arg Phe Tyr Gln Ser Leu Pro
        130                 135                 140

Gly Arg Thr Trp Gly Asp Val Met Ile Pro Ser Thr Met Ala Gly Asn
145                 150                 155                 160

Ala Trp Val Trp Ala Tyr Asn Tyr Cys Val Asn Asn Gln Gly Ala Ala
                165                 170                 175

Pro Leu Val Tyr Phe Gly Asn Pro Tyr Asp Ser Gln Ile Asp Ser Leu
                180                 185                 190

Leu Ala Met Gly Ala Asp Pro Phe Thr Gly Gly Ser Ile
                195                 200                 205

<210> SEQ ID NO 2
<211> LENGTH: 190
<212> TYPE: PRT
<213> ORGANISM: Bacteriophage

<400> SEQUENCE: 2

Met Val Lys Lys Asn Asp Leu Phe Val Asp Val Ser His Asn Gly
1               5                   10                  15

Tyr Asp Ile Thr Gly Ile Leu Glu Gln Met Gly Thr Thr Asn Thr Ile
                20                  25                  30

Ile Lys Ile Ser Glu Ser Thr Thr Tyr Leu Asn Pro Cys Leu Ser Ala
                35                  40                  45

Gln Val Glu Gln Ser Asn Pro Ile Gly Phe Tyr His Phe Ala Arg Phe
        50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
                100                 105                 110

Gln Met Ile Ala Asp Ala Gly Tyr Lys Pro Ile Tyr Tyr Ser Tyr Lys
                115                 120                 125

Pro Phe Thr His Asp Asn Val Asp Tyr Gln Gln Ile Leu Ala Gln Phe
                130                 135                 140

```
Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp
            180                 185                 190

<210> SEQ ID NO 3
<211> LENGTH: 146
<212> TYPE: PRT
<213> ORGANISM: Bacteriophage

<400> SEQUENCE: 3

Met Thr Thr Val Asn Glu Ala Leu Asn Asn Val Arg Ala Gln Val Gly
1               5                   10                  15

Ser Gly Val Ser Val Gly Asn Gly Glu Cys Tyr Ala Leu Ala Ser Trp
            20                  25                  30

Tyr Glu Arg Met Ile Ser Pro Asp Ala Thr Val Gly Leu Gly Ala Gly
                35                  40                  45

Val Gly Trp Val Ser Gly Ala Ile Gly Asp Thr Ile Ser Ala Lys Asn
    50                  55                  60

Ile Gly Ser Ser Tyr Asn Trp Gln Ala Asn Gly Trp Thr Val Ser Thr
65                  70                  75                  80

Ser Gly Pro Phe Lys Ala Gly Gln Ile Val Thr Leu Gly Ala Thr Pro
                85                  90                  95

Gly Asn Pro Tyr Gly His Val Val Ile Val Glu Ala Val Asp Gly Asp
            100                 105                 110

Arg Leu Thr Ile Leu Glu Gln Asn Tyr Gly Gly Lys Arg Tyr Pro Val
        115                 120                 125

Arg Asn Tyr Tyr Ser Ala Ala Ser Tyr Arg Gln Gln Val Val His Tyr
    130                 135                 140

Ile Thr
145

<210> SEQ ID NO 4
<211> LENGTH: 21
<212> TYPE: PRT
<213> ORGANISM: Bacteriophage

<400> SEQUENCE: 4

Thr Gly Asp Gly Lys Asn Pro Ser Val Gly Thr Gly Asn Ala Thr Val
1               5                   10                  15

Ser Ala Ser Ser Glu
            20

<210> SEQ ID NO 5
<211> LENGTH: 23
<212> TYPE: PRT
<213> ORGANISM: Bacteriophage

<400> SEQUENCE: 5

Thr Gly Asp Gly Lys Asn Pro Ser Val Gly Thr Gly Asn Ala Thr Val
1               5                   10                  15

Ser Ala Ser Ser Glu Cys Thr
            20

<210> SEQ ID NO 6
<211> LENGTH: 21
<212> TYPE: PRT
```

<213> ORGANISM: Bacteriophage

<400> SEQUENCE: 6

Gln Thr Asn Pro Asn Pro Asp Lys Pro Thr Val Lys Ser Pro Gly Gln
1               5                   10                  15

Asn Asp Leu Gly Ser
            20

<210> SEQ ID NO 7
<211> LENGTH: 23
<212> TYPE: PRT
<213> ORGANISM: Bacteriophage

<400> SEQUENCE: 7

Leu Gln Gln Thr Asn Pro Asn Pro Asp Lys Pro Thr Val Lys Ser Pro
1               5                   10                  15

Gly Gln Asn Asp Leu Gly Ser
            20

<210> SEQ ID NO 8
<211> LENGTH: 157
<212> TYPE: PRT
<213> ORGANISM: Bacteriophage

<400> SEQUENCE: 8

Gly Ser Asp Arg Val Ala Ala Asn Leu Ala Asn Ala Gln Ala Gln Val
1               5                   10                  15

Gly Lys Tyr Ile Gly Asp Gly Gln Cys Tyr Ala Trp Val Gly Trp Trp
            20                  25                  30

Ser Ala Arg Val Cys Gly Tyr Ser Ile Ser Tyr Ser Thr Gly Asp Pro
        35                  40                  45

Met Leu Pro Leu Ile Gly Asp Gly Met Asn Ala His Ser Ile His Leu
    50                  55                  60

Gly Trp Asp Trp Ser Ile Ala Asn Thr Gly Ile Val Asn Tyr Pro Val
65                  70                  75                  80

Gly Thr Val Gly Arg Lys Glu Asp Leu Arg Val Gly Ala Ile Trp Cys
                85                  90                  95

Ala Thr Ala Phe Ser Gly Ala Pro Phe Tyr Thr Gly Gln Tyr Gly His
            100                 105                 110

Thr Gly Ile Ile Glu Ser Trp Ser Asp Thr Val Thr Val Leu Glu
        115                 120                 125

Gln Asn Ile Leu Gly Ser Pro Val Ile Arg Ser Thr Tyr Asp Leu Asn
    130                 135                 140

Thr Phe Leu Ser Thr Leu Thr Gly Leu Ile Thr Phe Lys
145                 150                 155

<210> SEQ ID NO 9
<211> LENGTH: 220
<212> TYPE: PRT
<213> ORGANISM: Bacteriophage

<400> SEQUENCE: 9

Met Val Lys Lys Asn Asp Leu Phe Val Asp Val Ser Ser His Asn Gly
1               5                   10                  15

Tyr Asp Ile Thr Gly Ile Leu Glu Gln Met Gly Thr Thr Asn Thr Ile
            20                  25                  30

Ile Lys Ile Ser Glu Ser Thr Thr Tyr Leu Asn Pro Cys Leu Ser Ala
        35                  40                  45

-continued

Gln Val Glu Gln Ser Asn Pro Ile Gly Phe Tyr His Phe Ala Arg Phe
 50                  55                  60

Gly Gly Asp Val Ala Glu Ala Glu Arg Glu Ala Gln Phe Phe Leu Asp
 65                  70                  75                  80

Asn Val Pro Met Gln Val Lys Tyr Leu Val Leu Asp Tyr Glu Asp Asp
                 85                  90                  95

Pro Ser Gly Asp Ala Gln Ala Asn Thr Asn Ala Cys Leu Arg Phe Met
                100                 105                 110

Gln Met Ile Ala Asp Ala Gly Tyr Lys Pro Ile Tyr Tyr Ser Tyr Lys
            115                 120                 125

Pro Phe Thr His Asp Asn Val Asp Tyr Gln Gln Ile Leu Ala Gln Phe
130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Glu Glu
                180                 185                 190

Asp Asp Lys Pro Lys Thr Ala Gly Thr Trp Lys Gln Asp Ser Lys Gly
            195                 200                 205

Trp Trp Phe Arg Arg Asn Asn Gly Ser Phe Pro Tyr
210                 215                 220

<210> SEQ ID NO 10
<211> LENGTH: 61
<212> TYPE: PRT
<213> ORGANISM: Bacteriophage

<400> SEQUENCE: 10

Ala Asn Arg Glu Lys Leu Lys Lys Ala Leu Thr Asp Leu Phe Asn Asn
 1               5                  10                  15

Asn Leu Glu His Leu Ser Gly Glu Phe Tyr Gly Asn Gln Val Leu Asn
                 20                  25                  30

Ala Met Lys Tyr Gly Thr Ile Leu Lys Cys Asp Leu Thr Asp Asp Gly
            35                  40                  45

Leu Asn Ala Ile Leu Gln Leu Ile Ala Asp Val Asn Leu
 50                  55                  60

<210> SEQ ID NO 11
<211> LENGTH: 150
<212> TYPE: PRT
<213> ORGANISM: Bacteriophage

<400> SEQUENCE: 11

Met Glu Glu Asp Asp Lys Pro Lys Thr Ala Gly Thr Trp Lys Gln Asp
 1               5                  10                  15

Ser Lys Gly Trp Trp Phe Arg Arg Asn Asn Gly Ser Phe Pro Tyr Asn
                 20                  25                  30

Lys Trp Glu Lys Ile Gly Gly Val Trp Tyr Tyr Phe Asp Ser Lys Gly
            35                  40                  45

Tyr Cys Leu Thr Ser Glu Trp Leu Lys Asp Asn Glu Lys Trp Tyr Tyr
 50                  55                  60

Leu Lys Asp Asn Gly Ala Met Ala Thr Gly Trp Val Leu Val Gly Ser
 65                  70                  75                  80

Glu Trp Tyr Tyr Met Asp Asp Ser Gly Ala Met Val Thr Gly Trp Val
                 85                  90                  95

```
Lys Tyr Lys Asn Asn Trp Tyr Tyr Met Thr Asn Glu Arg Gly Asn Met
                100                 105                 110

Val Ser Asn Glu Phe Ile Lys Ser Gly Lys Gly Trp Tyr Phe Met Asn
            115                 120                 125

Thr Asn Gly Glu Leu Ala Asp Asn Pro Ser Phe Thr Lys Glu Pro Asp
        130                 135                 140

Gly Leu Ile Thr Val Ala
145                 150

<210> SEQ ID NO 12
<211> LENGTH: 149
<212> TYPE: PRT
<213> ORGANISM: Bacteriophage

<400> SEQUENCE: 12

Glu Glu Asp Asp Lys Pro Lys Thr Ala Gly Thr Trp Lys Gln Asp Ser
1               5                   10                  15

Lys Gly Trp Trp Phe Arg Arg Asn Asn Gly Ser Phe Pro Tyr Asn Lys
            20                  25                  30

Trp Glu Lys Ile Gly Gly Val Trp Tyr Tyr Phe Asp Ser Lys Gly Tyr
        35                  40                  45

Cys Leu Thr Ser Glu Trp Leu Lys Asp Asn Glu Lys Trp Tyr Tyr Leu
    50                  55                  60

Lys Asp Asn Gly Ala Met Ala Thr Gly Trp Val Leu Val Gly Ser Glu
65                  70                  75                  80

Trp Tyr Tyr Met Asp Asp Ser Gly Ala Met Val Thr Gly Trp Val Lys
                85                  90                  95

Tyr Lys Asn Asn Trp Tyr Tyr Met Thr Asn Glu Arg Gly Asn Met Val
                100                 105                 110

Ser Asn Glu Phe Ile Lys Ser Gly Lys Gly Trp Tyr Phe Met Asn Thr
            115                 120                 125

Asn Gly Glu Leu Ala Asp Asn Pro Ser Phe Thr Lys Glu Pro Asp Gly
        130                 135                 140

Leu Ile Thr Val Ala
145

<210> SEQ ID NO 13
<211> LENGTH: 104
<212> TYPE: PRT
<213> ORGANISM: Bacteriophage

<400> SEQUENCE: 13

Gly Thr Met Pro Pro Gly Thr Val Ala Gln Ser Ala Pro Asn Leu Ala
1               5                   10                  15

Gly Ser Arg Ser Tyr Arg Glu Thr Gly Thr Met Thr Val Thr Val Asp
            20                  25                  30

Ala Leu Asn Val Arg Arg Ala Pro Asn Thr Ser Gly Glu Ile Val Ala
        35                  40                  45

Val Tyr Lys Arg Gly Glu Ser Phe Asp Tyr Asp Thr Val Ile Ile Asp
    50                  55                  60

Val Asn Gly Tyr Val Trp Val Ser Tyr Ile Gly Gly Ser Gly Lys Arg
65                  70                  75                  80

Asn Tyr Val Ala Thr Gly Ala Thr Lys Asp Gly Lys Arg Phe Gly Asn
                85                  90                  95

Ala Trp Gly Thr Phe Lys Thr Ser
            100
```

<210> SEQ ID NO 14
<211> LENGTH: 100
<212> TYPE: PRT
<213> ORGANISM: Bacteriophage

<400> SEQUENCE: 14

Met Pro Pro Gly Thr Val Ala Gln Ser Ala Pro Asn Leu Ala Gly Ser
1               5                   10                  15

Arg Ser Tyr Arg Glu Thr Gly Thr Met Thr Val Thr Val Asp Ala Leu
            20                  25                  30

Asn Val Arg Arg Ala Pro Asn Thr Ser Gly Glu Ile Val Ala Val Tyr
        35                  40                  45

Lys Arg Gly Glu Ser Phe Asp Tyr Asp Thr Val Ile Ile Asp Val Asn
50                  55                  60

Gly Tyr Val Trp Val Ser Tyr Ile Gly Gly Ser Gly Lys Arg Asn Tyr
65                  70                  75                  80

Val Ala Thr Gly Ala Thr Lys Asp Gly Lys Arg Phe Gly Asn Ala Trp
                85                  90                  95

Gly Thr Phe Lys
            100

<210> SEQ ID NO 15
<211> LENGTH: 99
<212> TYPE: PRT
<213> ORGANISM: Bacteriophage

<400> SEQUENCE: 15

Pro Pro Gly Thr Val Ala Gln Ser Ala Pro Asn Leu Ala Gly Ser Arg
1               5                   10                  15

Ser Tyr Arg Glu Thr Gly Thr Met Thr Val Thr Val Asp Ala Leu Asn
            20                  25                  30

Val Arg Arg Ala Pro Asn Thr Ser Gly Glu Ile Val Ala Val Tyr Lys
        35                  40                  45

Arg Gly Glu Ser Phe Asp Tyr Asp Thr Val Ile Ile Asp Val Asn Gly
    50                  55                  60

Tyr Val Trp Val Ser Tyr Ile Gly Gly Ser Gly Lys Arg Asn Tyr Val
65                  70                  75                  80

Ala Thr Gly Ala Thr Lys Asp Gly Lys Arg Phe Gly Asn Ala Trp Gly
                85                  90                  95

Thr Phe Lys

<210> SEQ ID NO 16
<211> LENGTH: 465
<212> TYPE: PRT
<213> ORGANISM: Bacteriophage

<400> SEQUENCE: 16

Met Ser Lys Lys Tyr Thr Gln Gln Gln Tyr Glu Lys Tyr Leu Ala Gln
1               5                   10                  15

Pro Ala Asn Asn Thr Phe Gly Leu Ser Pro Gln Gln Val Ala Asp Trp
            20                  25                  30

Phe Met Gly Gln Ala Gly Ala Arg Pro Val Ile Asn Ser Tyr Gly Val
        35                  40                  45

Asn Ala Ser Asn Leu Val Ser Thr Tyr Ile Pro Lys Met Gln Glu Tyr
    50                  55                  60

Gly Val Ser Tyr Thr Leu Phe Leu Met Tyr Thr Val Phe Glu Gly Gly
65                  70                  75                  80

Gly Ala Gly Asn Trp Ile Asn His Tyr Met Tyr Asp Thr Gly Ser Asn
                85                  90                  95

Gly Leu Glu Cys Leu Glu His Asp Leu Gln Tyr Ile His Gly Val Trp
            100                 105                 110

Glu Thr Tyr Phe Pro Pro Ala Leu Ser Ala Pro Glu Cys Tyr Pro Ala
        115                 120                 125

Thr Glu Asp Asn Ala Gly Ala Leu Asp Arg Phe Tyr Gln Ser Leu Pro
    130                 135                 140

Gly Arg Thr Trp Gly Asp Val Met Ile Pro Ser Thr Met Ala Gly Asn
145                 150                 155                 160

Ala Trp Val Trp Ala Tyr Asn Tyr Cys Val Asn Asn Gln Gly Ala Ala
                165                 170                 175

Pro Leu Val Tyr Phe Gly Asn Pro Tyr Asp Ser Gln Ile Asp Ser Leu
            180                 185                 190

Leu Ala Met Gly Ala Asp Pro Phe Thr Gly Ser Ile Thr Gly Asp
        195                 200                 205

Gly Lys Asn Pro Ser Val Gly Thr Gly Asn Ala Thr Val Ser Ala Ser
    210                 215                 220

Ser Glu Ala Asn Arg Glu Lys Leu Lys Lys Ala Leu Thr Asp Leu Phe
225                 230                 235                 240

Asn Asn Asn Leu Glu His Leu Ser Gly Glu Phe Tyr Gly Asn Gln Val
                245                 250                 255

Leu Asn Ala Met Lys Tyr Gly Thr Ile Leu Lys Cys Asp Leu Thr Asp
            260                 265                 270

Asp Gly Leu Asn Ala Ile Leu Gln Leu Ile Ala Asp Val Asn Leu Gln
        275                 280                 285

Thr Asn Pro Asn Pro Asp Lys Pro Thr Val Lys Ser Pro Gly Gln Asn
    290                 295                 300

Asp Leu Gly Ser Gly Ser Asp Arg Val Ala Ala Asn Leu Ala Asn Ala
305                 310                 315                 320

Gln Ala Gln Val Gly Lys Tyr Ile Gly Asp Gly Gln Cys Tyr Ala Trp
                325                 330                 335

Val Gly Trp Trp Ser Ala Arg Val Cys Gly Tyr Ser Ile Ser Tyr Ser
            340                 345                 350

Thr Gly Asp Pro Met Leu Pro Leu Ile Gly Asp Gly Met Asn Ala His
        355                 360                 365

Ser Ile His Leu Gly Trp Asp Trp Ser Ile Ala Asn Thr Gly Ile Val
    370                 375                 380

Asn Tyr Pro Val Gly Thr Val Gly Arg Lys Glu Asp Leu Arg Val Gly
385                 390                 395                 400

Ala Ile Trp Cys Ala Thr Ala Phe Ser Gly Ala Pro Phe Tyr Thr Gly
                405                 410                 415

Gln Tyr Gly His Thr Gly Ile Ile Glu Ser Trp Ser Asp Thr Thr Val
            420                 425                 430

Thr Val Leu Glu Gln Asn Ile Leu Gly Ser Pro Val Ile Arg Ser Thr
        435                 440                 445

Tyr Asp Leu Asn Thr Phe Leu Ser Thr Leu Thr Gly Leu Ile Thr Phe
    450                 455                 460

Lys
465

<210> SEQ ID NO 17
<211> LENGTH: 512

<212> TYPE: PRT
<213> ORGANISM: Bacteriophage

<400> SEQUENCE: 17

```
Met Ser Lys Lys Tyr Thr Gln Gln Tyr Glu Lys Tyr Leu Ala Gln
1               5                   10                  15

Pro Ala Asn Asn Thr Phe Gly Leu Ser Pro Gln Val Ala Asp Trp
                20                  25                  30

Phe Met Gly Gln Ala Gly Ala Arg Pro Val Ile Asn Ser Tyr Gly Val
            35                  40                  45

Asn Ala Ser Asn Leu Val Ser Thr Tyr Ile Pro Lys Met Gln Glu Tyr
        50                  55                  60

Gly Val Ser Tyr Thr Leu Phe Leu Met Tyr Thr Val Phe Glu Gly Gly
65                  70                  75                  80

Gly Ala Gly Asn Trp Ile Asn His Tyr Met Tyr Asp Thr Gly Ser Asn
                85                  90                  95

Gly Leu Glu Cys Leu Glu His Asp Leu Gln Tyr Ile His Gly Val Trp
            100                 105                 110

Glu Thr Tyr Phe Pro Pro Ala Leu Ser Ala Pro Glu Cys Tyr Pro Ala
        115                 120                 125

Thr Glu Asp Asn Ala Gly Ala Leu Asp Arg Phe Tyr Gln Ser Leu Pro
    130                 135                 140

Gly Arg Thr Trp Gly Asp Val Met Ile Pro Ser Thr Met Ala Gly Asn
145                 150                 155                 160

Ala Trp Val Trp Ala Tyr Asn Tyr Cys Val Asn Asn Gln Gly Ala Ala
                165                 170                 175

Pro Leu Val Tyr Phe Gly Asn Pro Tyr Asp Ser Gln Ile Asp Ser Leu
            180                 185                 190

Leu Ala Met Gly Ala Asp Pro Phe Thr Gly Gly Ser Ile Met Glu Glu
        195                 200                 205

Asp Asp Lys Pro Lys Thr Ala Gly Thr Trp Lys Gln Asp Ser Lys Gly
    210                 215                 220

Trp Trp Phe Arg Arg Asn Asn Gly Ser Phe Pro Tyr Asn Lys Trp Glu
225                 230                 235                 240

Lys Ile Gly Gly Val Trp Tyr Tyr Phe Asp Ser Lys Gly Tyr Cys Leu
                245                 250                 255

Thr Ser Glu Trp Leu Lys Asp Asn Glu Lys Trp Tyr Tyr Leu Lys Asp
            260                 265                 270

Asn Gly Ala Met Ala Thr Gly Trp Val Leu Val Gly Ser Glu Trp Tyr
        275                 280                 285

Tyr Met Asp Asp Ser Gly Ala Met Val Thr Gly Trp Val Lys Tyr Lys
    290                 295                 300

Asn Asn Trp Tyr Tyr Met Thr Asn Glu Arg Gly Asn Met Val Ser Asn
305                 310                 315                 320

Glu Phe Ile Lys Ser Gly Lys Gly Trp Tyr Phe Met Asn Thr Asn Gly
                325                 330                 335

Glu Leu Ala Asp Asn Pro Ser Phe Thr Lys Glu Pro Asp Gly Leu Ile
            340                 345                 350

Thr Val Ala Gly Ser Asp Arg Val Ala Ala Asn Leu Ala Asn Ala Gln
        355                 360                 365

Ala Gln Val Gly Lys Tyr Ile Gly Asp Gly Gln Cys Tyr Ala Trp Val
    370                 375                 380

Gly Trp Trp Ser Ala Arg Val Cys Gly Tyr Ser Ile Ser Tyr Ser Thr
385                 390                 395                 400
```

```
Gly Asp Pro Met Leu Pro Leu Ile Gly Asp Gly Met Asn Ala His Ser
                405                 410                 415

Ile His Leu Gly Trp Asp Trp Ser Ile Ala Asn Thr Gly Ile Val Asn
            420                 425                 430

Tyr Pro Val Gly Thr Val Gly Arg Lys Glu Asp Leu Arg Val Gly Ala
        435                 440                 445

Ile Trp Cys Ala Thr Ala Phe Ser Gly Ala Pro Phe Tyr Thr Gly Gln
    450                 455                 460

Tyr Gly His Thr Gly Ile Ile Glu Ser Trp Ser Asp Thr Thr Val Thr
465                 470                 475                 480

Val Leu Glu Gln Asn Ile Leu Gly Ser Pro Val Ile Arg Ser Thr Tyr
                485                 490                 495

Asp Leu Asn Thr Phe Leu Ser Thr Leu Thr Gly Leu Ile Thr Phe Lys
                500                 505                 510

<210> SEQ ID NO 18
<211> LENGTH: 558
<212> TYPE: PRT
<213> ORGANISM: Bacteriophage

<400> SEQUENCE: 18

Met Ser Lys Lys Tyr Thr Gln Gln Tyr Glu Lys Tyr Leu Ala Gln
1               5                   10                  15

Pro Ala Asn Asn Thr Phe Gly Leu Ser Pro Gln Gln Val Ala Asp Trp
            20                  25                  30

Phe Met Gly Gln Ala Gly Ala Arg Pro Val Ile Asn Ser Tyr Gly Val
        35                  40                  45

Asn Ala Ser Asn Leu Val Ser Thr Tyr Ile Pro Lys Met Gln Glu Tyr
    50                  55                  60

Gly Val Ser Tyr Thr Leu Phe Leu Met Tyr Thr Val Phe Glu Gly Gly
65                  70                  75                  80

Gly Ala Gly Asn Trp Ile Asn His Tyr Met Tyr Asp Thr Gly Ser Asn
                85                  90                  95

Gly Leu Glu Cys Leu Glu His Asp Leu Gln Tyr Ile His Gly Val Trp
            100                 105                 110

Glu Thr Tyr Phe Pro Pro Ala Leu Ser Ala Pro Glu Cys Tyr Pro Ala
        115                 120                 125

Thr Glu Asp Asn Ala Gly Ala Leu Asp Arg Phe Tyr Gln Ser Leu Pro
    130                 135                 140

Gly Arg Thr Trp Gly Asp Val Met Ile Pro Ser Thr Met Ala Gly Asn
145                 150                 155                 160

Ala Trp Val Trp Ala Tyr Asn Tyr Cys Val Asn Asn Gln Gly Ala Ala
                165                 170                 175

Pro Leu Val Tyr Phe Gly Asn Pro Tyr Asp Ser Gln Ile Asp Ser Leu
            180                 185                 190

Leu Ala Met Gly Ala Asp Pro Phe Thr Gly Gly Ser Ile Thr Gly Asp
        195                 200                 205

Gly Lys Asn Pro Ser Val Gly Thr Gly Asn Ala Thr Val Ser Ala Ser
    210                 215                 220

Ser Glu Cys Thr Met Glu Glu Asp Asp Lys Pro Lys Thr Ala Gly Thr
225                 230                 235                 240

Trp Lys Gln Asp Ser Lys Gly Trp Trp Phe Arg Arg Asn Asn Gly Ser
                245                 250                 255

Phe Pro Tyr Asn Lys Trp Glu Lys Ile Gly Gly Val Trp Tyr Tyr Phe
```

```
                260                 265                 270
Asp Ser Lys Gly Tyr Cys Leu Thr Ser Glu Trp Leu Lys Asp Asn Glu
        275                 280                 285

Lys Trp Tyr Tyr Leu Lys Asp Asn Gly Ala Met Ala Thr Gly Trp Val
        290                 295                 300

Leu Val Gly Ser Glu Trp Tyr Tyr Met Asp Asp Ser Gly Ala Met Val
305                 310                 315                 320

Thr Gly Trp Val Lys Tyr Lys Asn Asn Trp Tyr Tyr Met Thr Asn Glu
                325                 330                 335

Arg Gly Asn Met Val Ser Asn Glu Phe Ile Lys Ser Gly Lys Gly Trp
            340                 345                 350

Tyr Phe Met Asn Thr Asn Gly Glu Leu Ala Asp Asn Pro Ser Phe Thr
        355                 360                 365

Lys Glu Pro Asp Gly Leu Ile Thr Val Ala Leu Gln Gln Thr Asn Pro
        370                 375                 380

Asn Pro Asp Lys Pro Thr Val Lys Ser Pro Gly Gln Asn Asp Leu Gly
385                 390                 395                 400

Ser Gly Ser Asp Arg Val Ala Ala Asn Leu Ala Asn Ala Gln Ala Gln
                405                 410                 415

Val Gly Lys Tyr Ile Gly Asp Gly Gln Cys Tyr Ala Trp Val Gly Trp
            420                 425                 430

Trp Ser Ala Arg Val Cys Gly Tyr Ser Ile Ser Tyr Ser Thr Gly Asp
        435                 440                 445

Pro Met Leu Pro Leu Ile Gly Asp Gly Met Asn Ala His Ser Ile His
        450                 455                 460

Leu Gly Trp Asp Trp Ser Ile Ala Asn Thr Gly Ile Val Asn Tyr Pro
465                 470                 475                 480

Val Gly Thr Val Gly Arg Lys Glu Asp Leu Arg Val Gly Ala Ile Trp
                485                 490                 495

Cys Ala Thr Ala Phe Ser Gly Ala Pro Phe Tyr Thr Gly Gln Tyr Gly
            500                 505                 510

His Thr Gly Ile Ile Glu Ser Trp Ser Asp Thr Thr Val Thr Val Leu
        515                 520                 525

Glu Gln Asn Ile Leu Gly Ser Pro Val Ile Arg Ser Thr Tyr Asp Leu
        530                 535                 540

Asn Thr Phe Leu Ser Thr Leu Thr Gly Leu Ile Thr Phe Lys
545                 550                 555

<210> SEQ ID NO 19
<211> LENGTH: 466
<212> TYPE: PRT
<213> ORGANISM: Bacteriophage

<400> SEQUENCE: 19

Met Ser Lys Lys Tyr Thr Gln Gln Tyr Glu Lys Tyr Leu Ala Gln
1               5                   10                  15

Pro Ala Asn Asn Thr Phe Gly Leu Ser Pro Gln Gln Val Ala Asp Trp
                20                  25                  30

Phe Met Gly Gln Ala Gly Ala Arg Pro Val Ile Asn Ser Tyr Gly Val
            35                  40                  45

Asn Ala Ser Asn Leu Val Ser Thr Tyr Ile Pro Lys Met Gln Glu Tyr
        50                  55                  60

Gly Val Ser Tyr Thr Leu Phe Leu Met Tyr Thr Val Phe Glu Gly Gly
65                  70                  75                  80
```

Gly Ala Gly Asn Trp Ile Asn His Tyr Met Tyr Asp Thr Gly Ser Asn
                85                  90                  95

Gly Leu Glu Cys Leu Glu His Asp Leu Gln Tyr Ile His Gly Val Trp
            100                 105                 110

Glu Thr Tyr Phe Pro Pro Ala Leu Ser Ala Pro Glu Cys Tyr Pro Ala
        115                 120                 125

Thr Glu Asp Asn Ala Gly Ala Leu Asp Arg Phe Tyr Gln Ser Leu Pro
    130                 135                 140

Gly Arg Thr Trp Gly Asp Val Met Ile Pro Ser Thr Met Ala Gly Asn
145                 150                 155                 160

Ala Trp Val Trp Ala Tyr Asn Tyr Cys Val Asn Asn Gln Gly Ala Ala
                165                 170                 175

Pro Leu Val Tyr Phe Gly Asn Pro Tyr Asp Ser Gln Ile Asp Ser Leu
            180                 185                 190

Leu Ala Met Gly Ala Asp Pro Phe Thr Gly Ser Ile Gly Thr Met
        195                 200                 205

Pro Pro Gly Thr Val Ala Gln Ser Ala Pro Asn Leu Ala Gly Ser Arg
    210                 215                 220

Ser Tyr Arg Glu Thr Gly Thr Met Thr Val Thr Val Asp Ala Leu Asn
225                 230                 235                 240

Val Arg Arg Ala Pro Asn Thr Ser Gly Glu Ile Val Ala Val Tyr Lys
                245                 250                 255

Arg Gly Glu Ser Phe Asp Tyr Asp Thr Val Ile Ile Asp Val Asn Gly
            260                 265                 270

Tyr Val Trp Val Ser Tyr Ile Gly Gly Ser Gly Lys Arg Asn Tyr Val
        275                 280                 285

Ala Thr Gly Ala Thr Lys Asp Gly Lys Arg Phe Gly Asn Ala Trp Gly
    290                 295                 300

Thr Phe Lys Thr Ser Gly Ser Asp Arg Val Ala Ala Asn Leu Ala Asn
305                 310                 315                 320

Ala Gln Ala Gln Val Gly Lys Tyr Ile Gly Asp Gly Gln Cys Tyr Ala
                325                 330                 335

Trp Val Gly Trp Trp Ser Ala Arg Val Cys Gly Tyr Ser Ile Ser Tyr
            340                 345                 350

Ser Thr Gly Asp Pro Met Leu Pro Leu Ile Gly Asp Gly Met Asn Ala
        355                 360                 365

His Ser Ile His Leu Gly Trp Asp Trp Ser Ile Ala Asn Thr Gly Ile
    370                 375                 380

Val Asn Tyr Pro Val Gly Thr Val Gly Arg Lys Glu Asp Leu Arg Val
385                 390                 395                 400

Gly Ala Ile Trp Cys Ala Thr Ala Phe Ser Gly Ala Pro Phe Tyr Thr
                405                 410                 415

Gly Gln Tyr Gly His Thr Gly Ile Ile Glu Ser Trp Ser Asp Thr Thr
            420                 425                 430

Val Thr Val Leu Glu Gln Asn Ile Leu Gly Ser Pro Val Ile Arg Ser
        435                 440                 445

Thr Tyr Asp Leu Asn Thr Phe Leu Ser Thr Leu Thr Gly Leu Ile Thr
    450                 455                 460

Phe Lys
465

<210> SEQ ID NO 20
<211> LENGTH: 508
<212> TYPE: PRT

<213> ORGANISM: Bacteriophage

<400> SEQUENCE: 20

Met Ser Lys Lys Tyr Thr Gln Gln Tyr Glu Lys Tyr Leu Ala Gln
1               5                   10                  15

Pro Ala Asn Asn Thr Phe Gly Leu Ser Pro Gln Gln Val Ala Asp Trp
            20                  25                  30

Phe Met Gly Gln Ala Gly Ala Arg Pro Val Ile Asn Ser Tyr Gly Val
        35                  40                  45

Asn Ala Ser Asn Leu Val Ser Thr Tyr Ile Pro Lys Met Gln Glu Tyr
    50                  55                  60

Gly Val Ser Tyr Thr Leu Phe Leu Met Tyr Thr Val Phe Glu Gly Gly
65                  70                  75                  80

Gly Ala Gly Asn Trp Ile Asn His Tyr Met Tyr Asp Thr Gly Ser Asn
                85                  90                  95

Gly Leu Glu Cys Leu Glu His Asp Leu Gln Tyr Ile His Gly Val Trp
            100                 105                 110

Glu Thr Tyr Phe Pro Pro Ala Leu Ser Ala Pro Glu Cys Tyr Pro Ala
        115                 120                 125

Thr Glu Asp Asn Ala Gly Ala Leu Asp Arg Phe Tyr Gln Ser Leu Pro
    130                 135                 140

Gly Arg Thr Trp Gly Asp Val Met Ile Pro Ser Thr Met Ala Gly Asn
145                 150                 155                 160

Ala Trp Val Trp Ala Tyr Asn Tyr Cys Val Asn Asn Gln Gly Ala Ala
                165                 170                 175

Pro Leu Val Tyr Phe Gly Asn Pro Tyr Asp Ser Gln Ile Asp Ser Leu
            180                 185                 190

Leu Ala Met Gly Ala Asp Pro Phe Thr Gly Gly Ser Ile Thr Gly Asp
        195                 200                 205

Gly Lys Asn Pro Ser Val Gly Thr Gly Asn Ala Thr Val Ser Ala Ser
    210                 215                 220

Ser Glu Cys Thr Met Pro Pro Gly Thr Val Ala Gln Ser Ala Pro Asn
225                 230                 235                 240

Leu Ala Gly Ser Arg Ser Tyr Arg Glu Thr Gly Thr Met Thr Val Thr
                245                 250                 255

Val Asp Ala Leu Asn Val Arg Arg Ala Pro Asn Thr Ser Gly Glu Ile
            260                 265                 270

Val Ala Val Tyr Lys Arg Gly Glu Ser Phe Asp Tyr Asp Thr Val Ile
        275                 280                 285

Ile Asp Val Asn Gly Tyr Val Trp Val Ser Tyr Ile Gly Gly Ser Gly
    290                 295                 300

Lys Arg Asn Tyr Val Ala Thr Gly Ala Thr Lys Asp Gly Lys Arg Phe
305                 310                 315                 320

Gly Asn Ala Trp Gly Thr Phe Lys Leu Gln Gln Thr Asn Pro Asn Pro
                325                 330                 335

Asp Lys Pro Thr Val Lys Ser Pro Gly Gln Asn Asp Leu Gly Ser Gly
            340                 345                 350

Ser Asp Arg Val Ala Ala Asn Leu Ala Asn Ala Gln Ala Gln Val Gly
        355                 360                 365

Lys Tyr Ile Gly Asp Gly Gln Cys Tyr Ala Trp Val Gly Trp Trp Ser
    370                 375                 380

Ala Arg Val Cys Gly Tyr Ser Ile Ser Tyr Ser Thr Gly Asp Pro Met
385                 390                 395                 400

```
Leu Pro Leu Ile Gly Asp Gly Met Asn Ala His Ser Ile His Leu Gly
            405                 410                 415

Trp Asp Trp Ser Ile Ala Asn Thr Gly Ile Val Asn Tyr Pro Val Gly
        420                 425                 430

Thr Val Gly Arg Lys Glu Asp Leu Arg Val Gly Ala Ile Trp Cys Ala
        435                 440                 445

Thr Ala Phe Ser Gly Ala Pro Phe Tyr Thr Gly Gln Tyr Gly His Thr
        450                 455                 460

Gly Ile Ile Glu Ser Trp Ser Asp Thr Thr Val Thr Val Leu Glu Gln
465                 470                 475                 480

Asn Ile Leu Gly Ser Pro Val Ile Arg Ser Thr Tyr Asp Leu Asn Thr
                485                 490                 495

Phe Leu Ser Thr Leu Thr Gly Leu Ile Thr Phe Lys
            500                 505

<210> SEQ ID NO 21
<211> LENGTH: 496
<212> TYPE: PRT
<213> ORGANISM: Bacteriophage

<400> SEQUENCE: 21

Met Val Lys Lys Asn Asp Leu Phe Val Asp Val Ser His Asn Gly
1               5                   10                  15

Tyr Asp Ile Thr Gly Ile Leu Glu Gln Met Gly Thr Thr Asn Thr Ile
            20                  25                  30

Ile Lys Ile Ser Glu Ser Thr Thr Tyr Leu Asn Pro Cys Leu Ser Ala
        35                  40                  45

Gln Val Glu Gln Ser Asn Pro Ile Gly Phe Tyr His Phe Ala Arg Phe
    50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
            100                 105                 110

Gln Met Ile Ala Asp Ala Gly Tyr Lys Pro Ile Tyr Tyr Ser Tyr Lys
        115                 120                 125

Pro Phe Thr His Asp Asn Val Asp Tyr Gln Gln Ile Leu Ala Gln Phe
    130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Glu Glu
            180                 185                 190

Asp Asp Lys Pro Lys Thr Ala Gly Thr Trp Lys Gln Asp Ser Lys Gly
        195                 200                 205

Trp Trp Phe Arg Arg Asn Asn Gly Ser Phe Pro Tyr Asn Lys Trp Glu
    210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Glu Lys Trp Tyr Tyr Leu Lys Asp
                245                 250                 255

Asn Gly Ala Met Ala Thr Gly Trp Val Leu Val Gly Ser Glu Trp Tyr
            260                 265                 270
```

```
Tyr Met Asp Asp Ser Gly Ala Met Val Thr Gly Trp Val Lys Tyr Lys
                275                 280                 285

Asn Asn Trp Tyr Tyr Met Thr Asn Glu Arg Gly Asn Met Val Ser Asn
            290                 295                 300

Glu Phe Ile Lys Ser Gly Lys Gly Trp Tyr Phe Met Asn Thr Asn Gly
305                 310                 315                 320

Glu Leu Ala Asp Asn Pro Ser Phe Thr Lys Glu Pro Asp Gly Leu Ile
                325                 330                 335

Thr Val Ala Gly Ser Asp Arg Val Ala Ala Asn Leu Ala Asn Ala Gln
                340                 345                 350

Ala Gln Val Gly Lys Tyr Ile Gly Asp Gly Gln Cys Tyr Ala Trp Val
                355                 360                 365

Gly Trp Trp Ser Ala Arg Val Cys Gly Tyr Ser Ile Ser Tyr Ser Thr
            370                 375                 380

Gly Asp Pro Met Leu Pro Leu Ile Gly Asp Gly Met Asn Ala His Ser
385                 390                 395                 400

Ile His Leu Gly Trp Asp Trp Ser Ile Ala Asn Thr Gly Ile Val Asn
                405                 410                 415

Tyr Pro Val Gly Thr Val Gly Arg Lys Glu Asp Leu Arg Val Gly Ala
                420                 425                 430

Ile Trp Cys Ala Thr Ala Phe Ser Gly Ala Pro Phe Tyr Thr Gly Gln
            435                 440                 445

Tyr Gly His Thr Gly Ile Ile Glu Ser Trp Ser Asp Thr Thr Val Thr
            450                 455                 460

Val Leu Glu Gln Asn Ile Leu Gly Ser Pro Val Ile Arg Ser Thr Tyr
465                 470                 475                 480

Asp Leu Asn Thr Phe Leu Ser Thr Leu Thr Gly Leu Ile Thr Phe Lys
                485                 490                 495

<210> SEQ ID NO 22
<211> LENGTH: 465
<212> TYPE: PRT
<213> ORGANISM: Bacteriophage

<400> SEQUENCE: 22

Met Thr Thr Val Asn Glu Ala Leu Asn Asn Val Arg Ala Gln Val Gly
1               5                   10                  15

Ser Gly Val Ser Val Gly Asn Gly Glu Cys Tyr Ala Leu Ala Ser Trp
                20                  25                  30

Tyr Glu Arg Met Ile Ser Pro Asp Ala Thr Val Gly Leu Gly Ala Gly
            35                  40                  45

Val Gly Trp Val Ser Gly Ala Ile Gly Asp Thr Ile Ser Ala Lys Asn
50                  55                  60

Ile Gly Ser Ser Tyr Asn Trp Gln Ala Asn Gly Trp Thr Val Ser Thr
65                  70                  75                  80

Ser Gly Pro Phe Lys Ala Gly Gln Ile Val Thr Leu Gly Ala Thr Pro
                85                  90                  95

Gly Asn Pro Tyr Gly His Val Val Ile Val Glu Ala Val Asp Gly Asp
                100                 105                 110

Arg Leu Thr Ile Leu Glu Gln Asn Tyr Gly Gly Lys Arg Tyr Pro Val
                115                 120                 125

Arg Asn Tyr Tyr Ser Ala Ala Ser Tyr Arg Gln Gln Val Val His Tyr
            130                 135                 140

Ile Thr Pro Pro Gly Thr Val Ala Gln Ser Ala Pro Asn Leu Ala Gly
```

```
145                 150                 155                 160
Ser Arg Ser Tyr Arg Glu Thr Gly Thr Met Thr Val Thr Val Asp Ala
            165                 170                 175

Leu Asn Val Arg Arg Ala Pro Asn Thr Ser Gly Glu Ile Val Ala Val
            180                 185                 190

Tyr Lys Arg Gly Glu Ser Phe Asp Tyr Asp Thr Val Ile Ile Asp Val
            195                 200                 205

Asn Gly Tyr Val Trp Val Ser Tyr Ile Gly Gly Ser Gly Lys Arg Asn
            210                 215                 220

Tyr Val Ala Thr Gly Ala Thr Lys Asp Gly Lys Arg Phe Gly Asn Ala
225                 230                 235                 240

Trp Gly Thr Phe Lys Met Val Lys Lys Asn Asp Leu Phe Val Asp Val
                245                 250                 255

Ser Ser His Asn Gly Tyr Asp Ile Thr Gly Ile Leu Glu Gln Met Gly
            260                 265                 270

Thr Thr Asn Thr Ile Ile Lys Ile Ser Glu Ser Thr Thr Tyr Leu Asn
            275                 280                 285

Pro Cys Leu Ser Ala Gln Val Glu Gln Ser Asn Pro Ile Gly Phe Tyr
    290                 295                 300

His Phe Ala Arg Phe Gly Gly Asp Val Ala Glu Ala Glu Arg Glu Ala
305                 310                 315                 320

Gln Phe Phe Leu Asp Asn Val Pro Met Gln Val Lys Tyr Leu Val Leu
                325                 330                 335

Asp Tyr Glu Asp Asp Pro Ser Gly Asp Ala Gln Ala Asn Thr Asn Ala
            340                 345                 350

Cys Leu Arg Phe Met Gln Met Ile Ala Asp Ala Gly Tyr Lys Pro Ile
        355                 360                 365

Tyr Tyr Ser Tyr Lys Pro Phe Thr His Asp Asn Val Asp Tyr Gln Gln
        370                 375                 380

Ile Leu Ala Gln Phe Pro Asn Ser Leu Trp Ile Ala Gly Tyr Gly Leu
385                 390                 395                 400

Asn Asp Gly Thr Ala Asn Phe Glu Tyr Phe Pro Ser Met Asp Gly Ile
            405                 410                 415

Arg Trp Trp Gln Tyr Ser Ser Asn Pro Phe Asp Lys Asn Ile Val Leu
            420                 425                 430

Leu Asp Asp Glu Glu Asp Asp Lys Pro Lys Thr Ala Gly Thr Trp Lys
            435                 440                 445

Gln Asp Ser Lys Gly Trp Trp Phe Arg Arg Asn Asn Gly Ser Phe Pro
    450                 455                 460

Tyr
465
```

DI-ENZYMATIC CHIMERIC ENDOLYSIN

CROSS REFERENCE TO RELATED APPLICATIONS

The application claims priority to U.S. Provisional Patent Application Ser. No. 62/755,869 filed Nov. 5, 2018, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, Md., 20899; voice (301) 301-975-2573; email tpo@nist.gov; reference application No. 16/598,144.

SEQUENCE LISTING

This application contains a Sequence Listing. CD-ROM discs Copy 1 and Copy 2 are identical, contain a copy of the Sequence Listing under 37 CFR Section 1.821 (e), and are read-only memory computer-readable compact discs. Each CD-ROM disc contains a copy of the Sequence Listing in ASCII text format. The Sequence Listing is named "19_011US1 Sequence Listing_ST25.txt." The copies of the Sequence Listing on the CD-ROM discs are hereby incorporated by reference in their entirety.

BRIEF DESCRIPTION

Disclosed is a di-enzymatic chimeric endolysin comprising: a primary enzymatic active domain disposed at an N-terminus end of the di-enzymatic chimeric endolysin, the primary enzymatic active domain comprising a primary protein sequence and that cleaves a glycosidic, peptide, or amide bond of the peptidoglycan in a cell wall of a cell; a secondary enzymatic active domain disposed at a C-terminus end of the di-enzymatic chimeric endolysin, the secondary enzymatic active domain comprising a secondary protein sequence and that, in combination with the primary enzymatic active domain, synergistically cleaves glycosidic, peptide, or amide bonds in the peptidoglycan in the cell wall; a cell wall binding domain: comprising a recognition sequence; chemically attached to the primary protein sequence and the secondary protein sequence, sequentially interposed between the primary protein sequence and the secondary protein sequence, and that binds to a cell wall; and a tertiary structure formed by folding of the primary protein sequence and the secondary protein sequence such that the primary enzymatic active domain faces and opposes the secondary enzymatic active domain in the di-enzymatic chimeric endolysin for synergistic cleavage of the peptidoglycan in the cell wall.

Disclosed is a process for lysing a cell with a di-enzymatic chimeric endolysin, the process comprising: contacting a cell wall of the cell with the di-enzymatic chimeric endolysin, the di-enzymatic chimeric endolysin comprising: a primary enzymatic active domain disposed at an N-terminus end of the di-enzymatic chimeric endolysin, the primary enzymatic active domain comprising a primary protein sequence and that cleaves a glycosidic, peptide, or amide bond of a peptidoglycan in a cell wall of a cell; a secondary enzymatic active domain disposed at a C-terminus end of the di-enzymatic chimeric endolysin, the secondary enzymatic active domain comprising a secondary protein sequence and that, in combination with the primary enzymatic active domain, synergistically cleaves glycosidic, peptide, or amide bonds in the peptidoglycan in the cell wall; a cell wall binding domain: comprising a recognition sequence; chemically attached to the primary protein sequence and the secondary protein sequence, sequentially interposed between the primary protein sequence and the secondary protein sequence, and that binds to a cell wall; and a tertiary structure formed by folding of the primary protein sequence and the secondary protein sequence such that the primary enzymatic active domain faces and opposes the secondary enzymatic active domain in the di-enzymatic chimeric endolysin for synergistic cleavage of the peptidoglycan in the cell wall; cleaving, by the primary enzymatic active domain, a first glycosidic, peptide, or amide bond of the peptidoglycan in the cell wall of the cell; cleaving, by the secondary enzymatic active domain, a second glycosidic, peptide, or amide bond of the peptidoglycan in the cell wall of the cell; and lysing the cell in response to cleaving the glycosidic, peptide, or amide bonds of the cell wall.

BRIEF DESCRIPTION OF THE DRAWINGS

The following description should not be considered limiting in any way. With reference to the accompanying drawings, like elements are numbered alike.

FIG. 15 shows minimal inhibitory concentrations (MICs) of endolysins and antibiotics for pneumococcal strains; and FIG. 16 shows MICs of endolysins and antibiotics for other streptococci strains.

DETAILED DESCRIPTION

Figure 1:
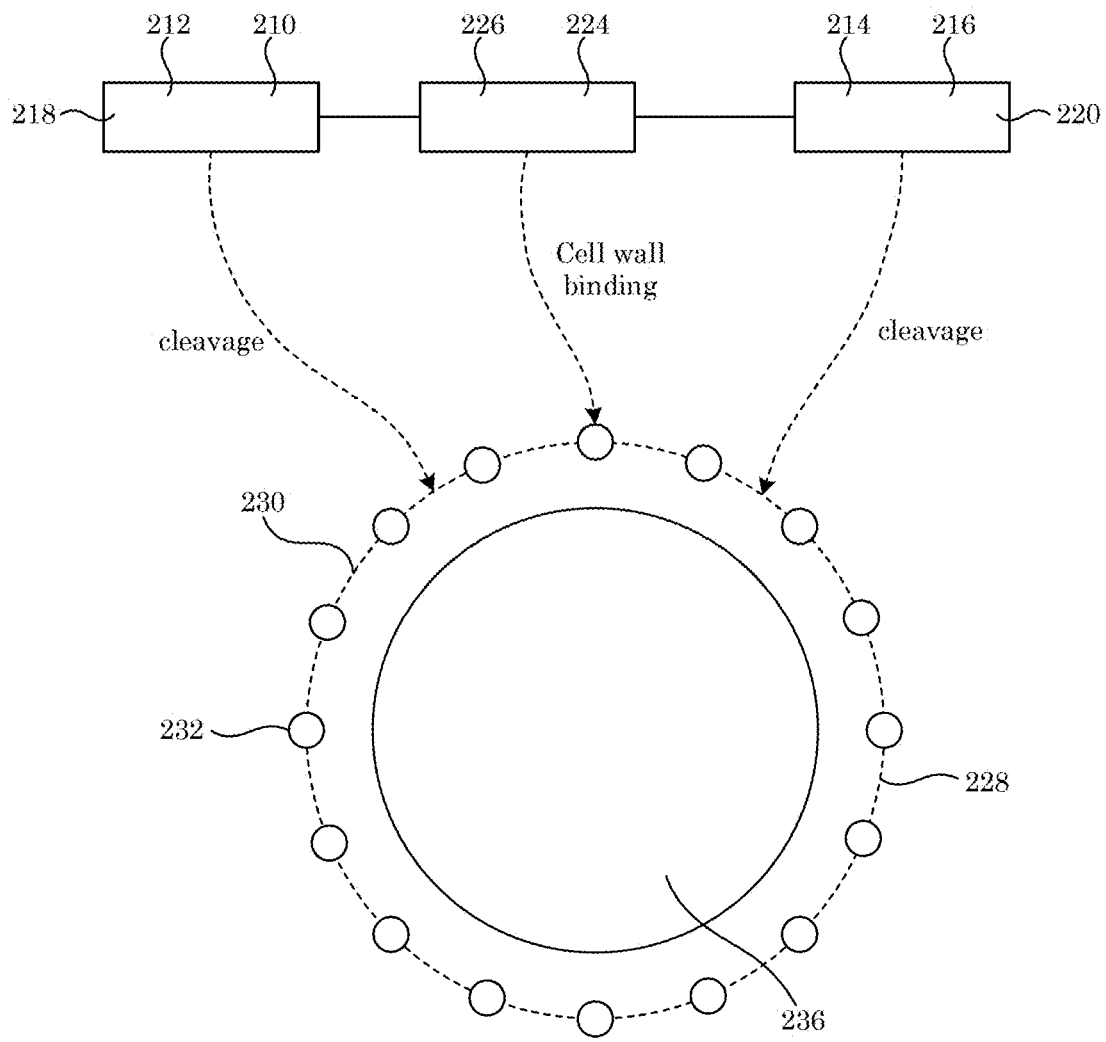
FIG. 1 shows a di-enzymatic chimeric endolysin.
Figure 2:
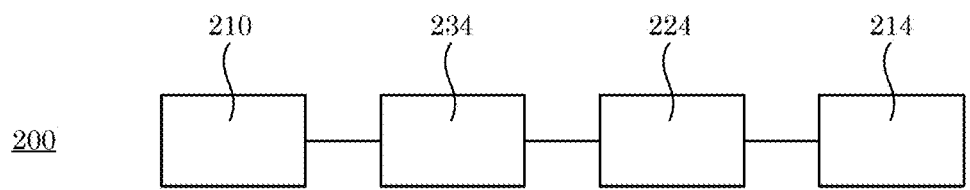
FIG. 2 shows a plurality of di-enzymatic chimeric endolysins.
Figure 2:
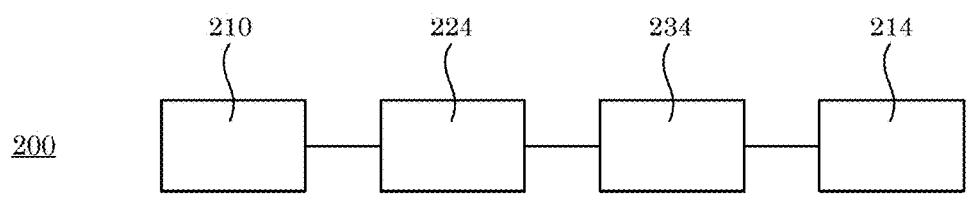
Figure 2:
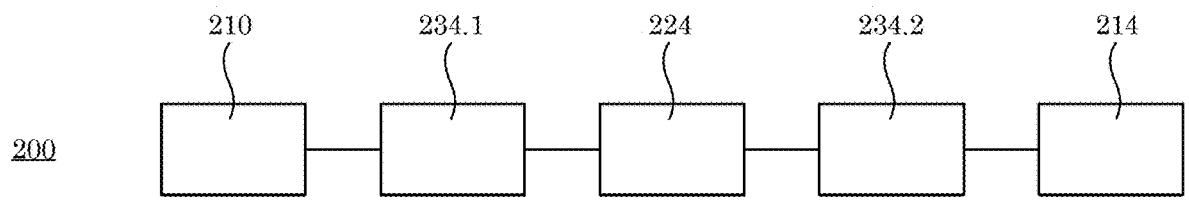

A detailed description of one or more embodiments is presented herein by way of exemplification and not limitation.

It has been discovered that a di-enzymatic chimeric endolysin and processes herein can include a bacteriophage-derived endolysin that is an alternative antimicrobial agent for Gram-positive bacterial infectious diseases. Advantageously, the di-enzymatic chimeric endolysin is a peptidoglycan hydrolase or lytic transglycosylase that destroys susceptible bacteria when applied exogenously. Due to the modular structure of the di-enzymatic chimeric endolysin, a process can select properties or a change of host range via change of functional domains. It is contemplated that the di-enzymatic chimeric endolysins can be chimeric endolysins. In vitro, the di-enzymatic chimeric endolysin had a 100-fold increase in activity against *S. pneumoniae* compared to the parental enzymes of the di-enzymatic chimeric endolysin. Other chimeric enzymes that were generated displayed broader host range, including acting on *Streptococcus mutans* and *Streptococcus agalacliae*. Furthermore, this design format can be applied to other enzymes in order to increase lytic activity.

Di-enzymatic chimeric endolysin 200 and processes herein lyses cell 236. In an embodiment, with reference to FIG. 1, FIG. 2, FIG. 3, and FIG. 4, di-enzymatic chimeric endolysin 200 includes: primary enzymatic active domain 212 disposed at the N-terminus end 218 end of di-enzymatic chimeric endolysin 200, primary enzymatic active domain 212 including primary protein sequence 210 that cleaves glycosidic bonds 230.1, peptide bonds 230.2, or amide bonds 230.3 of peptidoglycan 232 in cell wall 228 of cell 236; secondary enzymatic active domain 216 disposed at C-terminus end 220 of di-enzymatic chimeric endolysin 200, secondary enzymatic active domain 216 including secondary protein sequence 214 and that, in combination with primary enzymatic active domain 212, synergistically cleaves glycosidic bonds 230.1, peptide bonds 230.2, or amide bonds 230.3 in peptidoglycan 232 in cell wall 228; cell wall binding domain 224: including recognition sequence 226; chemically attached to primary protein sequence 210 and secondary protein sequence 214, sequentially interposed between primary protein sequence 210 and secondary protein sequence 214, and that binds to cell wall 228; and tertiary structure 222 formed by folding of primary protein sequence 210 and secondary protein sequence 214 such that primary enzymatic active domain 212 faces and opposes secondary enzymatic active domain 216 in di-enzymatic chimeric endolysin 200 for synergistic cleavage of peptidoglycan 232 in cell wall 228.

In an embodiment, di-enzymatic chimeric endolysin 200 includes first linker 234.1 interposed between primary protein sequence 210 and recognition sequence 226. In an embodiment, first linker 234.1 includes an amino acid sequence that is TGDGKNPSVGTGNATVSASSE (Sequence ID No. 4), TGDGKNPSVGTGNATVSASSECT (Sequence ID No. 5), or an amino acid sequence with a homology of at least 30% compared to the amino acid sequence for (Sequence ID No. 4) or (Sequence ID No. 5).

In an embodiment, di-enzymatic chimeric endolysin includes second linker 234.2 interposed between secondary protein sequence 214 and recognition sequence 226. Second linker 234.2 includes an amino acid sequence that is QTNPNPDKPTVKSPGQNDLGS (Sequence ID No. 6), LQQTNPNPDKPTVKSPGQNDLGS (Sequence ID No. 7), or an amino acid sequence with a homology of at least 30% compared to the amino acid sequence for (Sequence ID No. 6), or (Sequence ID No. 7).

In an embodiment, primary protein sequence 210 includes an amino acid sequence that is MSKKYTQQQYEKYLAQ-PANNTFGLSPQQVADWFMGQAGARPVINSYGV-NASNLVSTY IPKMQEYGVSYTLFLMYTVFEGGGAG-NWINHYMYDTGSNGLECLEHDLQYIHGVWET YFPPALSAPECYPATEDNAGALDRFYQSLPG-RTWGDVMIPSTMAGNAWVWAYNYCVN NQGAA-PLVYFGNPYDSQIDSLLAMGADPFTGGSI (Sequence ID No. 1), MVKKNDLFVDVSSHNGYDITG-ILEQMGTTNTIIKISESTTYLNPCLSAQVEQSN-PIGFYHF ARFGGDVAEAEREAQFFLDNVPMQVKYL-VLDYEDDPSGDAQANTNACLRFMQMIADA GYKPIYYSYKPFTHDNVDYQQILAQFPNSLWI-AGYGLNDGTANFEYFPSMDGIRWWQY SSNPFDKNIVLLDD (Sequence ID No. 2), MTTVNEAL- NNVRAQVGSGVSVGNGECYALASWYERMISP-DATVGLGAGVGWVSGAIG DTISAKNIGSSYN-WQANGWTVSTSGPFKAGQIVTLGATPGNPYGHVVI-VEAVDGDRLTI LEQNYGGKRYPVRNYYSAASYRQQ-VVHYIT (Sequence ID No. 3), or an amino acid sequence with a homology of at least 30% compared to the amino acid sequence for (Sequence ID No. 1), (Sequence ID No. 2), or (Sequence ID No. 3).

In an embodiment, secondary protein sequence 214 includes an amino acid sequence that is (Sequence ID No. 8)
GSDRVAANLANAQAQVGKYIGDGQCYAWVGWWSARVCGYSISYSTGDPMLP

LIGDGMNAHSIHLGWDWSIANTGIVNYPVGTVGRKEDLRVGAIWCATAFSG

APFYTGQYGHTGIIESWSDTTVTVLEQNILGSPVIRSTYDLNTFLSTLTGL

ITFK, (Sequence ID No. 9)
MVKKNDLFVDVSSHNGYDITGILEQMGTTNTIIKISESTTYLNPCLSAQVE

QSNPIGFYHFARFGGDVAEAEREAQFFLDNVPMQVKYLVLDYEDDPSGDAQ

ANTNACLRFMQMIADAGYKPIYYSYKPFTHDNVDYQQILAQFPNSLWIAGY

GLNDGTANFEYFPSMDGIRWWQYSSNPFDKNIVLLDDEEDDKPKTAGTWKQ

DSKGWWFRRNNGSFPY, or an amino acid sequence with a homology of at least 30% compared to the amino acid sequence for (Sequence ID No. 1), (Sequence ID No. 2), or (Sequence ID No. 3).

In an embodiment, recognition sequence 226 includes an amino acid sequence that is ANREKLKKALTDLFNNN-LEHLSGEFYGNQVLNAMKYGTILKCDLTDDG-LNAILQLIAD VNL (Sequence ID No. 10), MEEDDKPK-TAGTWKQDSKGWWFRRNNGSFPYNKWEKIGGVW-YYFDSKGYCLTSEWL KDNEKWYYLKDNGAMAT-GWV LVGSEWYYMDDSGAMVTGWVKYKNNWYY-MTNER GNMVSNEFIKSGKGWYFMNTNGE-LADNPSFTKEPDGLITVA (Sequence ID No. 11), EEDDKPKTAGTWKQDSKGWWFRRNNGSFPYNK-WEKIGGVWYYFDSKGYCLTSEWLK DNEKWYYL-KDNGAMATGWVLVGSEWYYMDDSGAMVTGWV-KYKNNWYYMTNERG NMVSNEFIKSGKGWYFM-NTNGELADNPSFTKEPDGLITVA (Sequence ID No. 12), or GTMPPGTVAQSAPNLAGSRSYRETGTMTVTV-DALNVRRAPNTSGEIVAVYKRGESFDY DTVI-IDVNGYVWVSYIGGSGKRNYVATGATKDGKRFG-NAWGTFKTS (Sequence ID No. 13), MPPGTVAQSAPN-LAGSRSYRETGTMTVTVDALNVRRAPNTSGEIVAV-YKRGESFDYDT VIIDVNGYVWVSYIGGSGKRNY-VATGATKDGKRFGNAWGTFK (Sequence ID No. 14), or PPGTVAQSAPNLAGSRSYRETGTMTVTVDALNVR-RAPNTSGEIVAVYKRGESFDYDTVI IDVNGYVWVSYIGGSGKRNYVATGATKDGKRFG-NAWGTFK (Sequence ID No. 15), or an amino acid sequence with a homology of at least 30% compared to the amino acid sequence for (Sequence ID No. 10), (Sequence ID No. 11), (Sequence ID No. 12), (Sequence ID No. 13), (Sequence ID No. 14), or (Sequence ID No. 15).

Figure 4:
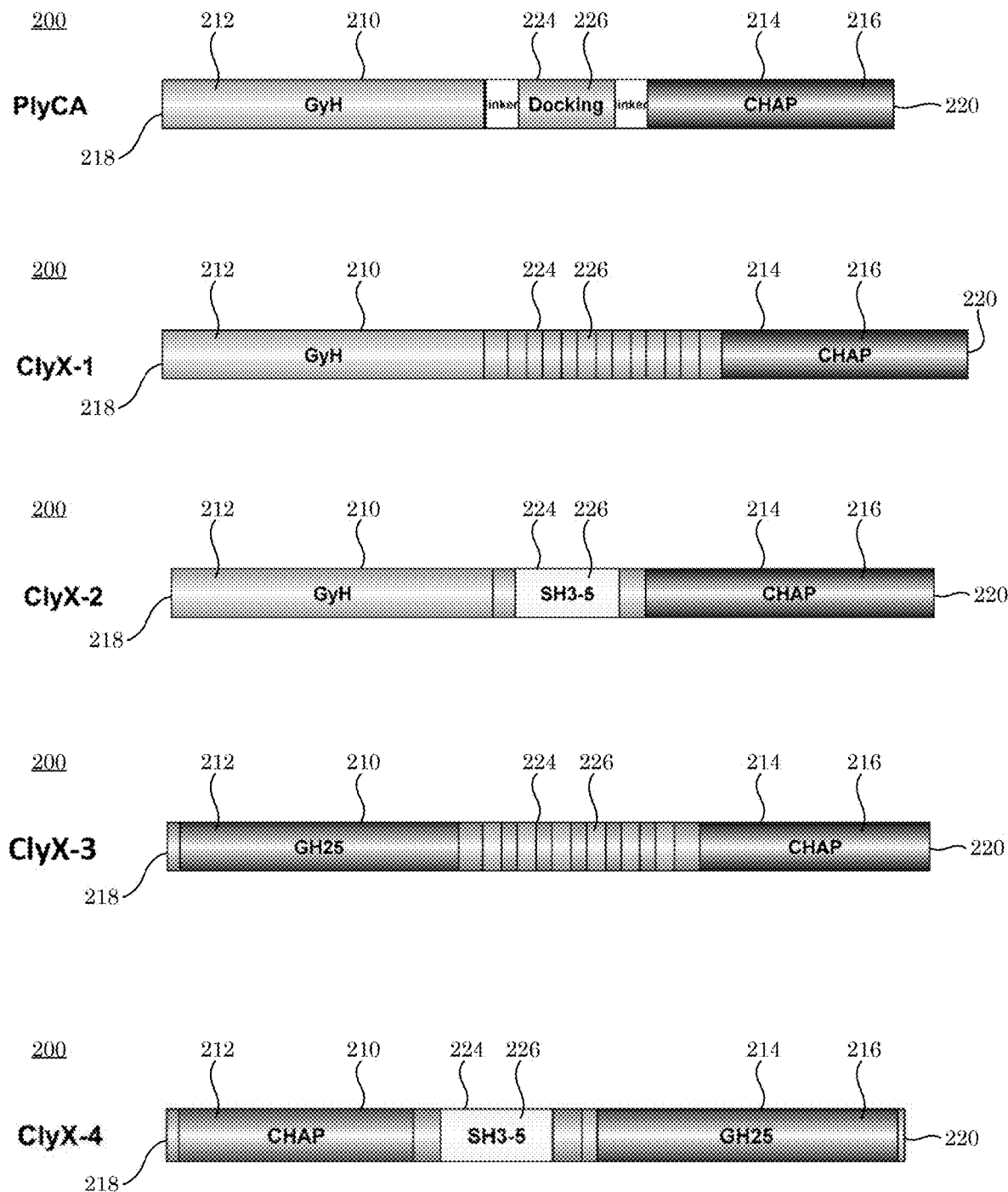
FIG. 4 shows a plurality of di-enzymatic chimeric endolysins.

With reference to Table 1 and FIG. 4, di-enzymatic chimeric endolysin 200 can include various components. In an embodiment, di-enzymatic chimeric endolysin 200 is ClyX-1, ClyX-2, ClyX-3, or ClyX-4.

In an embodiment, di-enzymatic chimeric endolysin 200 includes an amino acid sequence that is:

(Sequence ID No. 16)
MSKKYTQQQYEKYLAQPANNTFGLSPQQVADWFMGQAGARPVINSYGVNAS

NLVSTYIPKMQEYGVSYTLFLMYTVFEGGGAGNWINHYMYDTGSNGLECLE

HDLQYIHGVWETYFPPALSAPECYPATEDNAGALDRFYQSLPGRTWGDVMI

PSTMAGNAWVWAYNYCVNNQGAAPLVYFGNPYDSQIDSLLAMGADPFTGGS

ITGDGKNPSVGTGNATVSASSEANREKLKKALTDLFNNNLEHLSGEFYGNQ

VLNAMKYGTILKCDLTDDGLNAILQLIADVNLQTNPNPDKPTVKSPGQNDL

GSGSDRVAANLANAQAQVGKYIGDGQCYAWVGWWSARVCGYSISYSTGDPM

LPLIGDGMNAHSIHLGWDWSIANTGIVNYPVGTVGRKEDLRVGAIWCATAF

SGAPFYTGQYGHTGIIESWSDTTVTVLEQNILGSPVIRSTYDLNTFLSTLT

GLITFK, (Sequence ID No. 17)
MSKKYTQQQYEKYLAQPANNTFGLSPQQVADWFMGQAGARPVINSYGVNAS

NLVSTYIPKMQEYGVSYTLFLMYTVFEGGGAGNWINHYMYDTGSNGLECLE

HDLQYIHGVWETYFPPALSAPECYPATEDNAGALDRFYQSLPGRTWGDVMI

PSTMAGNAWVWAYNYCVNNQGAAPLVYFGNPYDSQIDSLLAMGADPFTGGS

IMEEDDKPKTAGTWKQDSKGWWFRRNNGSFPYNKWEKIGGVWYYFDSKGYC

LTSEWLKDNEKWYYLKDNGAMATGWVLVGSEWYYMDDSGAMVTGWVKYKNN

WYYMTNERGNMVSNEFIKSGKGWYFMNTNGELADNPSFTKEPDGLITVAGS

DRVAANLANAQAQVGKYIGDGQCYAWVGWWSARVCGYSISYSTGDPMLPLI

GDGMNAHSIHLGWDWSTANTGIVNYPVGTVGRKEDLRVGAIWCATAFSGAP

FYTGQYGHTGIIESWSDTTVTVLEQNILGSPVIRSTYDLNTFLSTLTGLIT

FK, (Sequence ID No. 18)
MSKKYTQQQYEKYLAQPANNTFGLSPQQVADWFMGQAGARPVINSYGVNAS

NLVSTYIPKMQEYGVSYTLFLMYTVFEGGGAGNWINHYMYDTGSNGLECLE

HDLQYIHGVWETYFPPALSAPECYPATEDNAGALDRFYQSLPGRTWGDVMI

PSTMAGNAWVWAYNYCVNNQGAAPLVYFGNPYDSQIDSLLAMGADPFTGGS

ITGDGKNPSVGTGNATVSASSECTMEEDDKPKTAGTWKQDSKGWWFRRNNG

SFPYNKWEKIGGVWYYFDSKGYCLTSEWLKDNEKWYYLKDNGAMATGWVLV

GSEWYYMDDSGAMVTGWVKYKNNWYYMTNERGNMVSNEFIKSGKGWYFMNT

NGELADNPSFTKEPDGLITVALQQTNPNPDKPTVKSPGQNDLGSGSDRVAA

NLANAQAQVGKYIGDGQCYAWVGWWSARVCGYSISYSTGDPMLPLIGDGMN

AHSIHLGWDWSIANTGIVNYPVGTVGRKEDLRVGAIWCATAFSGAPFYTGQ

YGHTGIIESWSDTTVTVLEQNILGSPVIRSTYDLNTFLSTLTGLITFK, (Sequence ID No. 19)
MSKKYTQQQYEKYLAQPANNTFGLSPQQVADWFMGQAGARPVINSYGVNAS

NLVSTYIPKMQEYGVSYTLFLMYTVFEGGGAGNWINHYMYDTGSNGLECLE

HDLQYIHGVWETYFPPALSAPECYPATEDNAGALDRFYQSLPGRTWGDVMI

PSTMAGNAWVWAYNYCVNNQGAAPLVYFGNPYDSQIDSLLAMGADPFTGGS

-continued

IGTMPPGTVAQSAPNLAGSRSYRETGTMTVTVDALNVRRAPNTSGEIVAVY

KRGESFDYDTVIIDVNGYVWVSYIGGSGKRNYVATGATKDGKRFGNAWGTF

KTSGSDRVAANLANAQAQVGKYIGDGQCYAWVGWWSARVCGYSISYSTGDP

MLPLIGDGMNAHSIHLGWDWSIANTGIVNYPVGTVGRKEDLRVGAIWCATA

FSGAPFYTGQYGHTGIIESWSDTTVTVLEQNILGSPVIRSTYDLNTFLSTL

TGLITFK, (Sequence ID No. 20)
MSKKYTQQQYEKYLAQPANNTFGLSPQQVADWFMGQAGARPVINSYGVNAS

NLVSTYIPKMQEYGVSYTLFLMYTVFEGGGAGNWINHYMYDTGSNGLECLE

HDLQYIHGVWETYFPPALSAPECYPATEDNAGALDRFYQSLPGRTWGDVMI

PSTMAGNAWVWAYNYCVNNQGAAPLVYFGNPYDSQIDSLLAMGADPFTGGS

ITGDGKNPSVGTGNATVSASSECTMPPGTVAQSAPNLAGSRSYRETGTMTV

TVDALNVRRAPNTSGEIVAVYKRGESFDYDTVIIDVNGYVWVSYIGGSGKR

NYVATGATKDGKRFGNAWGTFKLQQTNPNPDKPTVKSPGQNDLGSGSDRVA

ANLANAQAQVGKYIGDGQCYAWVGWWSARVCGYSISYSTGDPMLPLIGDGM

NAHSIHLGWDWSIANTGIVNYPVGTVGRKEDLRVGAIWCATAFSGAPFYTG

QYGHTGIIESWSDTTVTVLEQNILGSPVIRSTYDLNTFLSTLTGLITFK, (Sequence ID No. 21)
MVKKNDLFVDVSSHNGYDITGILEQMGTTNTIIKISESTTYLNPCLSAQVE

QSNPIGFYHFARFGGDVAEAEREAQFFLDNVPMQVKYLVLDYEDDPSGDAQ

ANTNACLRFMQMIADAGYKPIYYSYKPFTHDNVDYQQILAQFPNSLWIAGY

GLNDGTANFEYFPSMDGIRWWQYSSNPFDKNIVLLDDEEDDKPKTAGTWKQ

DSKGWWFRRNNGSFPYNKWEKIGGVWYYFDSKGYCLTSEWLKDNEKWYYLK

DNGAMATGWVLVGSEWYYMDDSGAMVTGWVKYKNNWYYMTNERGNMVSNEF

IKSGKGWYFMNTNGELADNPSFTKEPDGLITVAGSDRVAANLANAQAQVGK

YIGDGQCYAWVGWWSARVCGYSISYSTGDPMLPLIGDGMNAHSIHLGWDWS

IANTGIVNYPVGTVGRKEDLRVGAIWCATAFSGAPFYTGQYGHTGIIESWS

DTTVTVLEQNILGSPVIRSTYDLNTFLSTLTGLITFK, (Sequence ID No. 22)
MTTVNEALNNVRAQVGSGVSVGNGECYALASWYERMISPDATVGLGAGVGW

VSGAIGDTISAKNIGSSYNWQANGWTVSTSGPFKAGQIVTLGATPGNPYGH

VVIVEAVDGDRLTILEQNYGGKRYPVRNYYSAASYRQQVVHYITPPGTVAQ

SAPNLAGSRSYRETGTMTVTVDALNVRRAPNTSGEIVAVYKRGESFDYDTV

IIDVNGYVWVSYIGGSGKRNYVATGATKDGKRFGNAWGTFKMVKKNDLFVD

VSSHNGYDITGILEQMGTTNTIIKISESTTYLNPCLSAQVEQSNPIGFYHF

ARFGGDVAEAEREAQFFLDNVPMQVKYLVLDYEDDPSGDAQANTNACLRFM

QMIADAGYKPIYYSYKPFTHDNVDYQQILAQFPNSLWIAGYGLNDGTANFE

YFPSMDGIRWWQYSSNPFDKNIVLLDDEEDDKPKTAGTWKQDSKGWWFRRN

NGSFPY, or an amino acid sequence with a homology of at least 30% compared to the amino acid sequence for (Sequence ID No. 16), (Sequence ID No. 17), (Sequence ID No. 18), (Sequence ID No. 19), (Sequence ID No. 20), (Sequence ID No. 21), or (Sequence ID No. 22).

TABLE 1

| Exemplary element | name | Seq. ID No. |
| --- | --- | --- |
| primary protein sequence 210 | PlyCA GyH | 1 |
| primary protein sequence 210 | Cpl-1 gh25 | 2 |
| primary protein sequence 210 | PlySs2 CHAP | 3 |
| first linker 234.1 | | 4 |
| first linker 234.1 | | 5 |
| second linker 234.2 | PlyCA Linker 2 | 6 |
| second linker 234.2 | PlyCA Linker 2* | 7 |
| secondary protein sequence 214 | PlyCA CHAP | 8 |
| secondary protein sequence 214 | Cpl-1 gh25* | 9 |
| recognition sequence 226 | PlyCA lil | 10 |
| recognition sequence 226 | Cpl-1 CBD | 11 |
| recognition sequence 226 | Cpl-1 CBD* | 12 |
| recognition sequence 226 | PlySs2 CBD | 13 |
| recognition sequence 226 | PlySs2 CBD* | 14 |
| recognition sequence 226 | PlySs2 CBD** | 15 |
| di-enzymatic chimeric endolysin 200 | endolysin ClyX-1 | 17 |
| di-enzymatic chimeric endolysin 200 | endolysin ClyX-1* | 18 |
| di-enzymatic chimeric endolysin 200 | endolysin ClyX-2 | 19 |
| di-enzymatic chimeric endolysin 200 | endolysin ClyX-2* | 20 |
| di-enzymatic chimeric endolysin 200 | endolysin ClyX-3 | 21 |
| di-enzymatic chimeric endolysin 200 | endolysin ClyX-4 | 22 |

It is contemplated that cell 236 includes a bacterial cell. The bacterial cell can include a Gram-positive bacterium, e.g., a Gram-positive cocci or bacilli. Exemplary bacterial cells include a pneumococcus, *Staphylococcus, Streptococcus, Corynebacterium, Clostridium, Listeria, Bacillus, Cutibacterium, Lactococcus*, or a combination thereof. The bacterial cell can include a Gram-negative bacterium. Exemplary bacterial cells include *Escherichia, Salmonella, Shigella, Pseudomonas, Moraxella, Helicobacter, Stenotrophomonas, Bdellovibrio, Neisseria, Haemophilus, Klebsiella, Legionella, Pseudomonas, Proteus, Enterobacter, Serratia, Helicobacter*, and *Acinetobacter*.

Primary enzymatic active domain 212 and secondary enzymatic active domain 216 are amenable to N-terminus end 218 or C-terminus end 220, wherein "amenable" indicates the ability to retain functional bacteriolytic activity. Moreover, cell wall binding domain 224 is amenable to being sequentially interposed between primary protein sequence 210 and secondary protein sequence 214.

Linker 234 can include flexible residues, such as glycine or serine, so that the adjacent protein domains are free to move relative to one another. Linkers can be naturally occurring linkers found in native endolysin sequences or they can be synthetic constructs. An example of a synthetic sequence is $(GGGS)_n$ where n-repeats can be from 1 to 100, specifically 1 to 20, and more specifically 3 to 10. A total number of amino acids in linker 234 can be from 1 to 1000, specifically from 1 to 200, and more specifically from 5 to 50.

Amino acids in the amino acid sequences (Seq. ID Nos. 1-22) can include a naturally occurring amino acid, including alanine, arginine, asparagine, aspartate, cysteine, glutamate, glutamine, glycine, histidine, isoleucine, leucine, lysine, methionine, phenylalanine, proline, serine, threonine, tryptophan, tyrosine, and valine. While specific amino acid sequences are recited, it should be appreciated that derivatives of individual amino acids can be included or a selected substitution of an amino acid in a selected sequence can be made in primary protein sequence 210, linker 234, recognition sequence 22 , or secondary protein sequence 214 such that synergistic cleavage of glycosidic bonds 230.1, peptide bonds 230.2, or amide bonds 230.3 in peptidoglycan 232 is not rendered inoperative by the derivation or substitution. In this respect, such sequences that include a derivative or substitution can have a homology of at least 30% compared to the recited sequences (e.g., any of Seq. ID Nos. 1-22).

Figure 3:
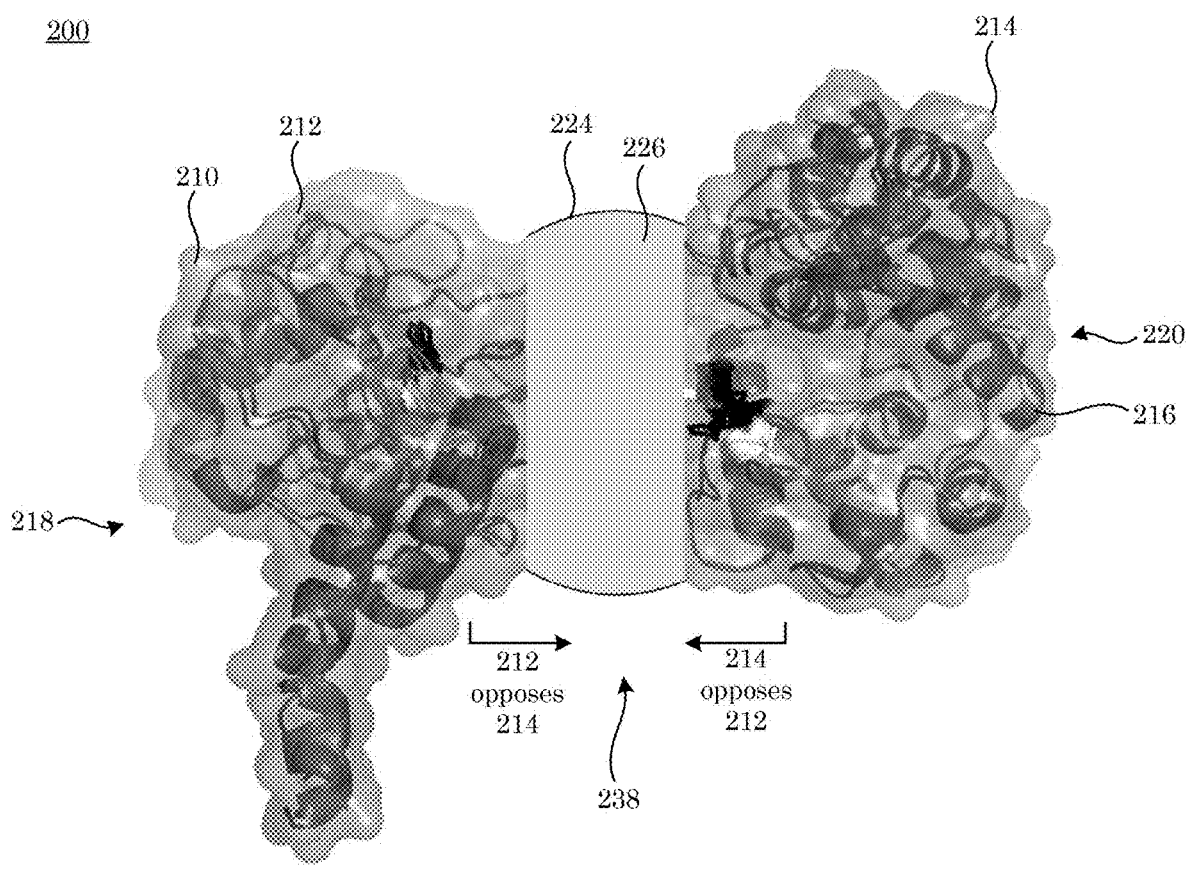
FIG. 3 shows a di-enzymatic chimeric endolysin.

With reference to FIG. 3, the sequence of amino acids in primary protein sequence 210, linker 234, recognition sequence 226, or secondary protein sequence 214 provide tertiary structure 222 that includes common groove 238, wherein common groove 238 is an outcome of primary enzymatic active domain 212 opposingly facing secondary enzymatic active domain 216. In di-enzymatic chimeric endolysin 200, primary enzymatic active domain 212 and secondary enzymatic active domain 216 cleave separate bonds synergistically. As used herein, "synergistic" as well as other forms of the word "synergistic" (e.g., synergy, synergistically, and the like) refers to the interaction or cooperation of two or more enzymatic active domains to produce a combined effect greater than the sum of their separate effects. In this regard, with reference to FIG. 1 and FIG. 5, secondary protein sequence 214 in combination with primary enzymatic active domain 212 synergistically cleaves glycosidic bonds 230.1, peptide bonds 230.2, or amide bonds 230.3 in peptidoglycan 232, e.g., peptidoglycan 232 in cell wall 228.

Figure 5:
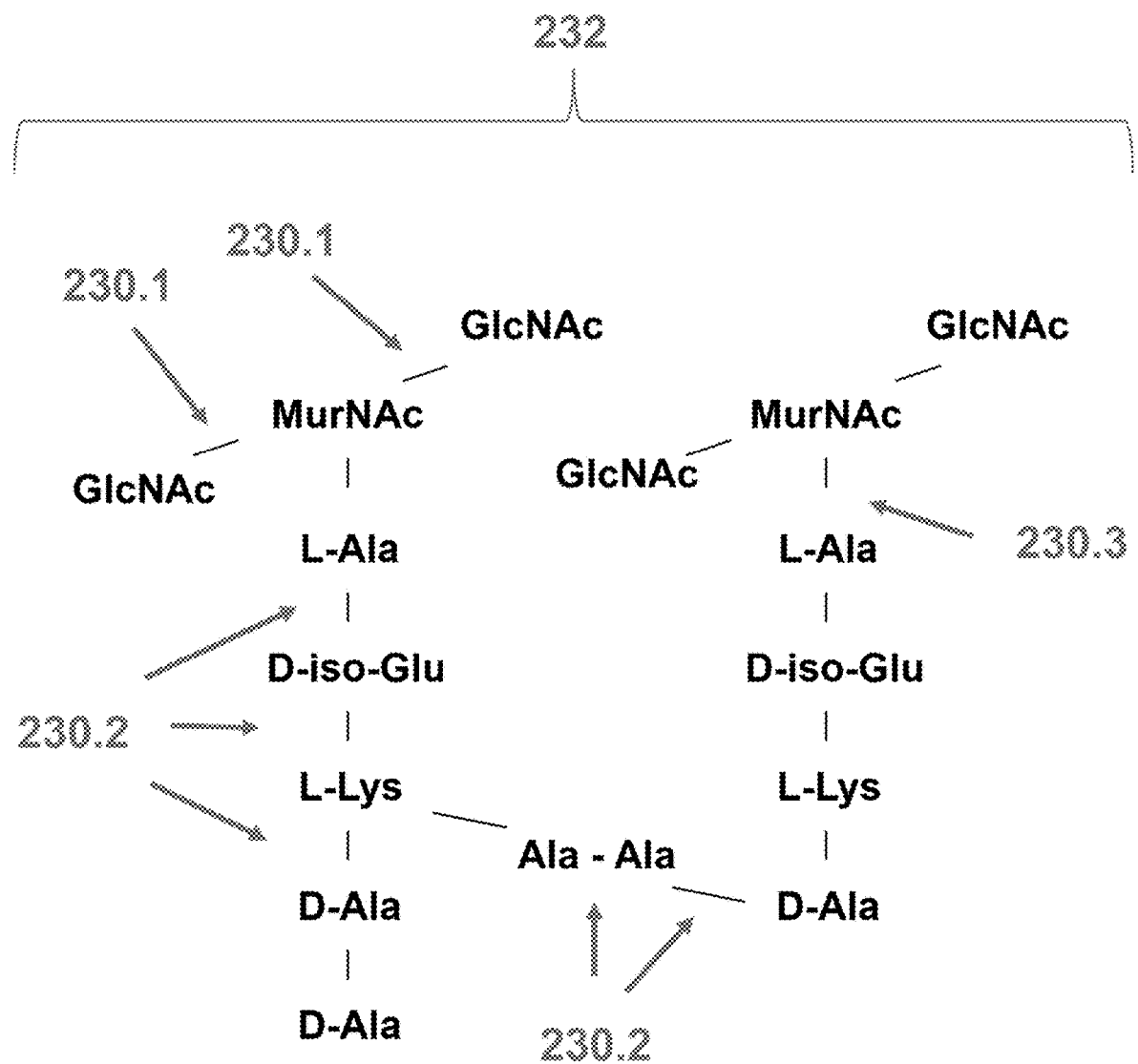
FIG. 5 shows synergistic cleavage of glyosidic, peptide, or amide bonds.

Peptidoglycan 232 is a structural unit of a bacterial cell wall and is a three dimensional lattice that includes peptide and glycan moieties. A polymer of alternating N-acetylmuramic acid (MurNAc) and N-acetylglucosamine (GlcNAc) residues coupled by β(1→4) glycosidic linkages is part of the glycan component of peptidoglycan 232 (FIG. 5). This polymer displays may have variation between bacterial species. The glycan polymer is covalently linked to a stem peptide through an amide bond between MurNAc and an L-alanine, the first amino acid of the peptide component. The remainder of the stem peptide includes alternating L- and D-form amino acids that are linked by peptide bonds and can be conserved in Gram-negative organisms but can be variable in composition for Gram-positive organisms. For some Gram-positive organisms, a third residue of the stem peptide is L-lysine, which is crosslinked to an opposing stem peptide on a separate glycan polymer through an interpeptide bridge, the composition of which can vary between species. For example, the interpeptide bridge of *Staphylococcus aureus* includes five glycine residues. The interpeptide bridge of *Streptococcus pyogenes* is two alanine residues (depicted in FIG. 5). In Gram-negative organisms and some genera of Gram-positive bacteria (i.e., *Bacillus* and *Listeria*), a meso-diaminopimelic acid (mDAP) residue is present at position number three of the stem peptide instead of L-lysine. In these organisms, mDAP directly crosslinks to the terminal D-alanine of the opposite stem peptide (i.e., no interpeptide bridge). An exemplary structure of peptidoglycan 232, specifically a peptidoglycan of *S. pyogenes*, is shown in FIG. 5.

Depending on the particular bond that is cleaved within peptidoglycan 232, endolysin enzymatic active domains (212 and 216) can be categorized in different groups, including those that cleave glycosidic bonds 230.1, those that cleave peptide bonds 230.2, and those that cleave amide bonds 230.3. (FIG. 5). N-acetylmuramidases, lytic transglycosylases, and N-acetyl-β-D-glucosaminidases cleave glycosidic bonds 230.1. N-acetylmuramidases (i.e., lysozymes) and lytic transglycosylases cleave the N-acetylmuramoyl-β-1,4-N-acetylglucosamine bond, which an alternating glycosidic bond of the glycan moiety. Another glycosidic bond in the glycan strand is cleaved by N-acetyl-β-D-glucosaminidases, which cleaves the N-acetylglucosaminyl-β-1,4-N-acetylmuramic acid bond. Peptide bonds 230.2 are formed between two amino acids, which can be present in the stem peptide or the interpeptide bridge, which are cleaved by endopeptidases. An amide bond 230.3 can be present between MurNAc of the glycan moiety and the L-alanine of the stem-peptide, which is cleaved by an L-acetylmuramoyl-L-alanine amidase.

According to the International Union of Biochemistry and Molecular Biology (IUBMB) enzyme nomenclature, glucosaminidases, muramidases, L-alanine-amidases, and endopeptidases are classified as hydrolases. Additionally, glucosaminidases and muramidases are further termed glycosidases or glycosol hydrolases. Lytic transglycosylases are not hydrolases, and an intramolecular interaction cleaves the glycosidic bond between N-acetylmuramoyl-β-1,4-N-acetylgluocosamine by formation of a concomitant 1,6-anhydromuramoyl product.

Due to the conservation in the enzyme activity domain sequences and structures of endolysins, databases have grouped these domains into specific families. These subgroups relate to the mechanisms for which the cleavage occurs rather than the specific bond cleaved. For example, the cysteine/histidine-dependent amidohydrolase/peptidase domains, referred to as CHAP domains, are an endolysin family that uses a cleavage mechanism, wherein a cysteine is deprotonated by a histidine, promoting a nucleophilic attack by the cysteine on the scissile bond. Some CHAP domains can display amidase activity, and some CHAP domains have endopeptidase specificity, cleaving between the terminal D-alanine of the stem peptide and the adjacent amino acid of the interpeptide bridge.

Di-enzymatic chimeric endolysin 200 can be made in various ways such as those described in the Example section. The process for making di-enzymatic chimeric endolysin 200 also can be formed by molecular biology techniques that can include cloning that uses vector-based multiple cloning sites that can join chimeric endolysins. In some embodiments, overlap extension polymerase chain reaction (OE-PCR) or splicing by overhang extension PCR (SOE-PCR) adds multiple, disparate domains into a single coding sequence to make di-enzymatic chimeric endolysin 200. Nucleic acid coding sequence for a di-enzymatic chimeric endolysin 200 can be designed in silico and synthesized de novo by DNA synthesis.

Di-enzymatic chimeric endolysin 200 has numerous advantageous and unexpected benefits and uses. In an embodiment, a process for lysing cell 236 with di-enzymatic chimeric endolysin 200 includes: contacting cell wall 228 of cell 236 with di-enzymatic chimeric endolysin 200; cleaving, by primary enzymatic active domain 212 a glycosidic bond 230.1, peptide bond 230.2, or amide bond 230.3, of peptidoglycan 232 in cell wall 228 of cell 236; cleaving, by secondary enzymatic active domain 216, a different glycosidic bond 230.1, peptide bond 230.2, or amide bond 230.3 of peptidoglycan 232 in cell wall 228 of cell 236; and lysing cell 236 in response to cleaving glycosidic bonds 230.1, peptide bonds 230.2, or amide bonds 230.3 of cell wall 228, wherein the combination of cleavage activity with primary enzymatic active domain 212 and secondary enzymatic active domain 216 occurs synergistically.

The process also can include administering di-enzymatic chimeric endolysin 200 to a subject. Exemplary subjects include humans, animals, agriculture products, aquiculture, feed stocks, abiotic or biotic surfaces for decontamination purposes, and the like. A route of administration can be selected with a suitable delivery mode. In this regard, the delivery mode can be, e.g., a pharmaceutical composition that includes di-enzymatic chimeric endolysin 200. In a pharmaceutical composition, di-enzymatic chimeric endolysin 200 can be isolated in any level of purity by, e.g., distillation, recrystallization, chromatography, and the like. Di-enzymatic chimeric endolysin 200 can be administered alone or in combination with pharmaceutically acceptable carriers or diluents, and such administration may be carried out in single or multiple doses. Compositions can be, e.g., in a form of tablets, pills sachets, vials, hard or soft capsules, aqueous or oily suspensions, aqueous or oily solutions, emulsions, powders, granules, syrups, elixirs, lozenges, reconstitutable powders, liquid preparations, creams, troches, hard candies, sprays, salves, suppositories, jellies, gels, pastes, lotions, injectable solutions, ointments, liquid aerosols, dry powder formulations, HFA aerosols, organic or inorganic acid addition salts, and the like. Di-enzymatic chimeric endolysin 200 can be in a form suitable for administration through oral, parenteral, subcutaneous, intravenous, intramuscular, buccal, or for administration by inhalation or insufflation (e.g. nasal, tracheal, bronchial) routes. Depending upon a disorder or patient to be treated and route of administration, the compositions can be administered at varying doses. Exemplary disorders include pneumococcal *pneumoniae*, staphylococcal bacteremia, acne vulgaris, and the like.

For oral, buccal, or sublingual administration, the compounds of di-enzymatic chimeric endolysin 200 can be combined with various excipients. Solid pharmaceutical preparations for oral administration can include a binding agent (e.g., syrups and sugars, acacia, gelatin, sorbitol, tragacanth, polyvinylpyrrolidone, sodium lauryl sulphate, pregelatinized maize starch, hydroxypropyl methylcellulose, lactose, starches, modified starches, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, sodium alginate, and the like), disintegrants (such as starch and preferably corn, potato or tapioca starch, alginic acid and certain complex silicates, polyvinylpyrrolidone, sucrose, gelatin, acacia, sodium starch glycollate, microcrystalline cellulose, crosscarmellose sodium, crospovidone, hydroxypropyl methylcellulose, hydroxypropyl cellulose, and the like), lubricating agents (such as magnesium stearate, sodium lauryl sulfate, talc, silica polyethylene glycol waxes, stearic acid, palmitic acid, calcium stearate, carnuba wax, hydrogenated vegetable oils, mineral oils, polyethylene glycols, sodium stearyl fumarate, and the like), fillers (including high molecular weight polyethylene glycols, lactose, sugar, calcium phosphate, sorbitol, glycine magnesium stearate, starch, glucose, lactose, sucrose, rice flour, chalk, gelatin, microcrystalline cellulose, calcium sulphate, xylitol, lactitol, and the like), and the like. Such preparations can include preservative agents and anti-oxidants.

Liquid compositions of di-enzymatic chimeric endolysin 200 for oral administration can be in the form, e.g., of emulsions, syrups, or elixirs, or can be presented as a dry product for reconstitution with water or other suitable vehicle before use. Such liquid compositions can include additives such as suspending agents (e.g., sorbitol, syrup, methyl cellulose, hydrogenated edible fats, gelatin, hydroxyalkylcelluloses, carboxymethylcellulose, aluminum stearate gel, hydrogenated edible fats, and the like), emulsifying agents (e.g., lecithin, sorbitan monooleate, acacia, and the like), aqueous or non-aqueous vehicles (including edible oils, e.g., almond oil, fractionated coconut oil, and the like), oily esters (e.g., esters of glycerine, propylene glycol, polyethylene glycol, ethyl alcohol, and the like), glycerine, water or normal saline, preservatives (e.g., methyl or propyl p-hydroxybenzoate, sorbic acid, and the like), flavoring, preservative, sweetening or coloring agents, and the like. Diluents such as water, ethanol, propylene glycol, glycerin, and the like can be included also.

For intranasal administration or administration by inhalation, the compounds of di-enzymatic chimeric endolysin 200 can be delivered in a form of a solution, dry powder, or suspension. Administration can occur by a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide, or other suitable gas. The compounds of di-enzymatic chimeric endolysin 200 can be administered via a dry powder inhaler, e.g., as a finely divided powder in combination with a carrier substance (e.g., a saccharide) or as microspheres. The inhaler, pump spray or aerosol spray can be single or multi dose. The dosage can be controlled through a valve which delivers a measured amount of active compound.

Parenteral (I.V. and I.M.) administration is contemplated. Here, compounds of di-enzymatic chimeric endolysin 200 can be formulated in an injectable form in an aqueous or non-aqueous solution, suspension or emulsion in a pharmaceutically acceptable liquid, e.g. sterile water, 1,3-butanediol, or a parenterally acceptable oil or a mixture of liquids. The liquid can include bacteriostatic agents, anti-oxidants or other preservatives, buffers, solutes, thickening agents, wetting agents, suspending agents, or other pharmaceutically acceptable additives. The composition can be a liquid that is isotonic with blood (e.g., through the addition of salts or glucose), e.g., with a pH>8. The liquid is dispensed into unit doses in the form of ampoules, disposable injection devices or vials. The formulation can be in the form of a concentrate or a dry preparation that can be reconstituted before use to prepare an injectable formulation.

With regard to a controlled, delayed, or prolonged release formulation of di-enzymatic chimeric endolysin 200, di-enzymatic chimeric endolysin 200 can be administered in a controlled release formulation. Such can be released at a selected rate to maintain constant pharmacological activity for a selected period. Such dosage forms provide a supply of di-enzymatic chimeric endolysin 200 to the body during a selected period and maintain an amount of di-enzymatic chimeric endolysin 200 in a therapeutic range for longer periods of time than a non-controlled formulation. Di-enzymatic chimeric endolysin 200 can be formulated in controlled release formulations in which release of di-enzymatic chimeric endolysin 200 is targeted. Release of di-enzymatic chimeric endolysin 200 can occur in a limited, specific region of the digestive system through pH sensitivity of the formulation.

The active di-enzymatic chimeric endolysin 200 can be administered in the form of liposome delivery systems such as small unilamellar vesicles, large unilamellar vesicles, or multilamellar vesicles. Liposomes can be formed from a variety of phospholipids such as cholesterol, stearylamine, or phosphatidylcholines.

The process for lysing cell 236 also can occur through osmotic lysis due to relatively high internal turgor pressure within bacterial cells relative to the outside environment. Notably, the degradation of the peptidoglycan renders cell 236 susceptible to this pressure gradient.

Di-enzymatic chimeric endolysin 200 and processes disclosed herein have numerous beneficial uses, including, due to their rapid lytic actions, endolysins are not susceptible to efflux pumps, penicillin binding proteins, alterations of metabolic pathways, or other mechanisms of resistance seen with conventional antibiotics, making them an advantageous therapeutic to treat multi-drug resistant organisms. Additionally, endolysins are species-specific, and as such, represent a potential narrow spectrum antimicrobial therapeutic that exploits the targeted killing capability of the bacteriophage from which the endolysin was derived. Advantageously, di-enzymatic chimeric endolysin 200 overcomes limitations of technical deficiencies of conventional endolysin compositions in that the additional enzymatically active domain provides synergistic activity with the first enzymatically active domain.

Beneficially, di-enzymatic chimeric endolysin 200 are antimicrobial and are a human therapeutic for treating an existing infection of prophylactically preventing an infection. Additionally, bacteria infect other animals, including companion animals to humans and food-producing animals such as livestock. It is contemplated that di-enzymatic chimeric endolysin 200 is an active agent for dairy cows, chickens, pigs, horses, and the like. As a disinfectant, di-enzymatic chimeric endolysin 200 can be contacted with a textile (e.g., cloth, fibers, and the like) or construction element (e.g., drywall, paint, and the like) to make antimicrobial articles.

The articles and processes herein are illustrated further by the following Example, which is non-limiting.

EXAMPLE

A Novel Design to Exploit the Synergy of PlyC Catalytic Domains

A bacteriophage-derived endolysin can be an antimicrobial agent for Gram-positive bacterial infectious diseases as they are peptidoglycan hydrolases or lytic transglycosylases that can destroy susceptible bacteria when applied exogenously. Due to the modular structure of endolysins, engineering methods can be used to improve their properties or change their host range via manipulation of the functional domains. The multimeric endolysin, PlyC, has potent activity on groups A, C, and E streptococci, as well as *Streptococcus uberis*, but is devoid of activity on other streptococci such as *S. agalactiae* (i.e., group B strep), *S. mutans*, or *S. pneumoniae*. PlyCA, the enzymatically active domain of PlyC, includes two catalytic domains, GyH, a glycosyl hydrolase, and CHAP, a cysteine, histidine-dependent amidohydrolase/peptidase. Notably, GyH and CHAP have been shown to work synergistically to achieve lytic rates ~100 fold higher than comparable single catalytic domain endolysins. A new design of chimeric endolysins take advantage of the synergistic effects of PlyCA. ClyX-1 was made via fusing the pneumococcal Cpl-1 cell binding domain (CBD) in between the GyH and CHAP catalytic domains of PlyCA. This chimera displayed ~100 fold increase in activity in vitro against *S. pneumoniae* and improved activity in vivo compared to the parental Cpl-1 enzyme. ClyX-2 was made using by fusing the broad host range PlySs2 CBD between GyH and CHAP catalytic domains. ClyX-2 demonstrated wild-type PlyC activities on groups A, C and E streptococci and included high levels of activity against *S. mutans* and *S. agalactiae*. Moreover, this design format (i.e., CBD in the middle of two catalytic domains) can also be applied to other enzymes in order to achieve improved activity. CHAP or GH25 catalytic domains were added to the C-terminus of full-length Cpl-1 and PlySs2, respectively, and displayed synergistic effects. To date, with the exception of PlyC, two catalytic domains in one endolysin have not shown synergism, even in enzymes that naturally contained two catalytic domains. This Example includes novel design for synergy of two catalytic domains for increased lytic activity.

The *Streptococcus* is a genus of Gram-positive bacteria consisting of diverse species distributed across the normal flora of human and animals. Although some generally cause no harm or are carried asymptomatically, most species are highly virulent and known to cause significant diseases. *Streptococcus mutans*, *Streptococcus pyogenes* (GAS), *Streptococcus agalactiae* (GBS), and *Streptococcus pneumoniae* are particularly notable as causative agents of serious acute infections in human, ranging from dental caries and pharyngitis to life-threatening conditions such as necrotizing fasciitis and meningitis. As animal pathogens, group C streptococci (GCS), group E streptococci (GES), *Streptococcus uberis*, and *Streptococcus suis* infect major livestock (i.e., cattle, pigs, and horses) leading to considerable economic significance to farmers. Due to the widespread distribution of antibiotic-resistance genes and overuse of broad-spectrum antibiotics, streptococci that used to sensitive to conventional antibiotics start developing resistant phenotypes. In a report published by Centers for Disease Control (CDC 2013), drug-resistant *Streptococcus pneumoniae* has been labeled as a "serious" public health threat as well as erythromycin-resistant GAS and clindamycin-resistant GBS as "concerning" public health threats. The emergence of resistant streptococci calls the need to source alternative antimicrobial agents.

Bacteriophage-encoded endolysins is an alternative treatment. Endolysins, also known as phage lysins or enzybiotics, are peptidoglycan (PG) hydrolases (or lytic transglycosylases) produced at the end of the phage reproduction cycle resulting in cell lysis and new phage release. When applied exogenously, these enzymes can destroy the Gram-positive bacterial PG rapidly and specifically. Endolysins derived from phage that infects Gram-positive hosts have modular structures with the enzymatically-active domain(s) at the N-terminus and a cell-binding domain (CBD) at the C-terminus. The EADs are capable of cleaving specific covalent bonds in the PG network to damage the intrinsic structural integrity. The CBDs possess no enzymatic activity but rather function to bind a specific substrate, usually a carbohydrate or teichoic acid attached to the host PG.

Several streptococcal endolysins have been discovered and investigated for enzymatical activity, structure-related characteristics, and in vivo safety and efficiency. PlyC, an endolysin from streptococcal C1 phage, displays the most remarkable activity ~100 fold that of the other lysins. Unlike other endolysins, PlyC is the only multimeric structured endolysin consisting of nine subunits—eight CBDs (PlyCB) to one EAD (PlyCA) encoding from two genes. Previous research has shown that PlyCB is specific for GAS, GCS, GES and *Streptococcus uberis*, limiting the PlyC activity against these species. Moreover, such high activity of PlyC is due to the two catalytic domains, N-terminal glycoside hydrolase (GyH) and C-terminal cysteine, histidine-dependent amidohydrolase/peptidase, working synergistically resulting from the positioning. Another well-studied endolysin is derived from the streptococcal Cp-1 phage, Cpl-1, whose CBD containing six repeated choline binding domains specifically binds to the choline on the teichoic acid of pneumococci. This enzyme has been validated to efficiently protect rats from pneumoniae-induced endocarditis and meningitis. Another streptococcal endolysin possessing broad host range is known as PlySs2, derived from *Streptococcus suis* phage. It displays lytic activity against multiple species of different bacterial pathogens, especially methicillin-resistant *Staphylococcus aureus* (MRSA).

Structure-based rational engineering has produced endolysins. Chimeragenesis is a potential engineering approach that has been successfully exploited by nature itself, such as pneumococcal endolysin Pal whose EAD and CBD indicated homology to different phage species. Engineering chimeras through domains shuffling have also been shown to be useful for extending specificity and increasing activity. For example, one streptococcal chimera, ClyR, the combination of PlyCA CHAP as EAD and PlySs2 CBD, retains the host range of PlySs2 with extension to *Streptococcus mutans*. The other example is the pneumococcal chimera, Cpl-711, the combination of Cpl-7 EAD and Cpl-1 CBD, displays much higher activity and stability than the parental enzymes.

Given the unique structure and high activity of PlyC, there is much interest in creating PlyCA chimeras with different CBDs to both take advantage of the synergistic effect and expanding its host range. Here, we provide three modular designs to use both domains of PlyCA as EAD with a choline specific binding domain from Cpl-1 and a broad host binding domain from PlySs2. By doing so, we were able to create ClyX-1 and ClyX-2 with the design that contains two EADs at each side of the Cpl-1 CBD/PlySs2 CBD. These two chimeras were able to exploit the synergy of GyH and CHAP dramatically increasing the activities. Furthermore, applying the design could also create the chimera with the additive effect of two EADs cutting different sites. Collectively, through generating the PlyCA chimeras, we figured a new modular design of domain swapping with two EADs to generate synergistic effect potentially.

The bacterial strains were stored at −80° C. as frozen stock in 20% glycerol, and are described in Table 1, which lists bacterial strains. Streptococcal strains were cultivated in Todd Hewitt broth supplemented with 1% (wt/vol of yeast extract without shaking. *Bacillus* strains were grown in brain heart infusion broth. All other bacterial strains including staphylococci and enterococci were cultured in tryptic soy broth (TSB). *E. coli* strains DH5a and BL21(DE3) were cultured in Luria-Bertani (LB) broth supplemented with 50 µg/mL carbenicillin or kanamycin as needed. Unless otherwise stated, bacterial strains were propagated at 37° C. and shaken at 200 rpm.

TABLE 1

| Organism | Serotype | Strain | Notes |
| --- | --- | --- | --- |
| *Bacillus cereus* | | 4342 | |
| *Enterococcus faecalis* | | JH2-2 | |
| *Enterococcus faecalis* | | EF-1 | Van$^R$ |
| *Enterococcus faecalis* | | EF-17 | Van$^R$ |
| *Enterococcus faecalis* | | EF-24 | |
| *Enterococcus faecalis* | | EF-25 | |
| *Enterococcus faecium* | | EFSK2 | Van$^R$ |
| *Enterococcus faecium* | | EFSK16 | Van$^R$ |
| *Enterococcus faecium* | | EFSK33 | Van$^R$ |
| Group E *streptococci* | 2 | K131 | Group E *streptococcus* |
| *Staphylococcus aureus* | | NR5385 | MRSA, MDR, USA500 |
| *Staphylococcus aureus* | | NRS14 | VISA |
| *Streptococcus agalactiae* | Type III | A909 | Group B *streptococcus* |
| *Streptococcus agalactiae* | Type IA | A349 | Group B *streptococcus* |
| *Streptococcus agalactiae* | Type IB | A934 | Group B *streptococcus* |
| *Streptococcus dysagalactiae* subs. *equisimilis* | | 21597 | Group C *streptococcus* |
| *Streptococcus equi* | | 9528 | Group C *streptococcus* |
| *Streptococcus equi* subs. *zooepidemicus* | | 700400 | Group C *streptococcus* |
| *Streptococcus mutans* | Type c | 10449 | |
| *Streptococcus mutans* | Type c | 25175 | |
| *Streptococcus mutans* | Type e | LM7 | |
| *Streptococcus pneumoniae* | 11 | DCC1811 | |
| *Streptococcus pneumoniae* | 15 | DCC1476 | |
| *Streptococcus pneumoniae* | 23F (Sp23-1) | DCC1420 | |
| *Streptococcus pneumoniae* | 19 | DCC1355 | |
| *Streptococcus pneumoniae* | 14 (Sp14-3) | DCC1494 | |
| *Streptococcus pneumoniae* | 6 | DCC1850 | |
| *Streptococcus pneumoniae* | 14 | DCC1490 | |
| *Streptococcus pneumoniae* | 3 | DCC1714 | |
| *Streptococcus pneumoniae* | 9V (Sp9-3) | DCC1335 | |
| *Streptococcus pneumoniae* | Derived from D39. Capsule free strain. | R36A | |
| *Streptococcus pneumoniae* | Derived from R36A. Capsule free strain. | R6 | |
| *Streptococcus pneumoniae* | | 765 | |
| *Streptococcus pneumoniae* | | #8 | |
| *Streptococcus pneumoniae* | | 763 | |
| *Streptococcus pneumoniae* | 2 | D39 | |
| *Streptococcus pneumoniae* | 4 | TIGR 4 | |
| *Streptococcus pneumoniae* | 18 | GB2017 | |
| *Streptococcus pneumoniae* | 1 | AR620 | |
| *Streptococcus pneumoniae* | 10 | GB2163 | |
| *Streptococcus pneumoniae* | 4 | GB2092 | |
| *Streptococcus pneumoniae* | 5 | AR314 | |
| *Streptococcus pneumoniae* | Derived from R6. LytA is non-functional. | Lyt4.4 | |

TABLE 1-continued

| Organism | Serotype | Strain | Notes |
|---|---|---|---|
| Streptococcus pyogenes | | MGAS315 | Group A streptococcus |
| Streptococcus pyogenes | M6 | D471 | Group A streptococcus |
| Streptococcus pyogenes | A-variant strain | A486 | Group A streptococcus |
| Streptococcus rattus | | BHT | |
| Streptococcus suis | | 7-3008-2 | |
| Streptococcus uberis | | BAA-854 | |
| Streptococcus uberis | | 700407 | |
| Streptococcus uberis | | 27958 | |
| Streptococus sobrinus | | 6715 | |

Plasmids and primers used in this study are listed in Table 2. Plasmid constructs for pBAD24::plyC, pBAD24::plyCA, pBAD24::plyCAGyH and pBAD24::plyCACHAP were cloned. Cpl-1 was cloned into pBAD24, and PlySs2 were codon-optimized for expression in *E. coli* and chemically synthesized. Primers were designed with 20 amino acid overlapped at each end of the connected pieces. First, each part of the chimeras was amplified through PCR to equip with the overlapping sequencing. Then, the resulting PCR fragments were fused and amplified again by PCR-based Gene Splicing by Overlap Extension PCR (SOE PCR). For constructions contain three gene pieces (clyX-1, clyX-1 Linkers, clyX-2), another round of SOE PCR was performed. After obtaining the final recombinant gene products, they were inserted via NdeI/BamHI sites into pET28a vector and cultured on LB plates supplemented with 50 μg/mL kanamycin. The resistant colonies were again picked and verified by DNA sequencing before being transformed into the expression strain BL21 (DE3).

kanamycin (50 μg/mL). The culture was shaken at 200 rpm at 37° C. for 3.5 h to reach $OD_{600}$=0.8. Proteins were induced using 0.25% (wt/vol) of L-arabinose for pBAD24 constructs or 0.1 mM isopropyl β-D-thiogalactoside (IPTG) for pET28a (+) constructs at 18° C. for another 20 h. Cells were pelleted at 5000 rpm for 15 min at 4° C. and stored at −80° C. before sonication. Frozen pellets were thawed in lysis buffer (PBS, pH 7.4, PBS, pH 7.4, supplemented with 1 mM phenylmethanesulfonyl fluoride (PMSF) and 10 mM imidazole) with shaking until dissolved completely. Sonication was then applied to lyse cells on ice for 15 min. The cell debris was removed via centrifugation at 12,000 rpm for 1 h at 4° C. The soluble portion containing recombinant proteins was passed through a nickel-nitrilotriacetic acid (Ni-NTA) column and fractions were collected from eluted buffers (PBS, pH7.4, supplemented with 20, 50, 100, 250, and 500 mM imidazole). After verified by SDS-PAGE analysis with Coomassie stain, the fractions containing recombinant proteins were dialyzed against PBS, pH 7.4,

TABLE 2

| Plasmid | Relevant properties |
|---|---|
| pBAD24 | Cloning and expression containing the arabinose PBAD promoter |
| pBAD24::cpl-1 | cpl-1gene of pneumococcal phage CP-1 cloned into pBAD24 |
| pBAD24::plyC | plyC operon gene of streptococcal phage $C_1$ cloned into SmaI/HindIII sites of pBAD24 |
| pBAD24::plyCA | plyCA gene of streptococcal phage $C_1$ cloned into SmaI/HindIII sites of pBAD24 |
| pBAD24::plySs2 | Chemical synthesis of lysin gene from *S. suis* strain 89/1591 |
| pET28a(+) | Cloning and expression containing N'6XHIS tag and the T7 promoter |
| pET28a(+)::clyX-1 | GyH ($PlyCA_{1-205}$), Cpl-1 $CBD_{(191-339)}$ and CHAP ($PlyCA_{309-465}$), fused via 2 round of SOE PCR cloned into NdeI/BamHI sites of pET28a(+) |
| pET28a(+)::clyX-1 Linkers | GyH with linker ($PlyCA_{1-227}$), Cpl-1 $CBD_{(191-339)}$ and CHAP with linker ($PlyCA_{287-465}$), fused via 2 round of SOE PCR cloned into NdeI/BamHI sites of pET28a(+) |
| pET28a(+)::clyX-2 | GyH ($PlyCA_{1-205}$), PlySs2 $CBD_{(148-245)}$ and CHAP ($PlyCA_{309-465}$), fused via 2 round of SOE PCR cloned into NdeI/BamHI sites of pET28a(+) |
| pET28a(+)::cpl-1 CBD_CHAP | Cpl-1 $CBD_{(191-339)}$ and CHAP ($PlyCA_{309-465}$), amplified using pET28a(+)::clyX-1 as template, cloned into NdeI/BamHI sites of pET28a(+) |
| pET28a(+)::cpl-1_CHAP | Cpl-1 full length and CHAP ($PlyCA_{309-465}$), fused via 2 round of SOE PCR cloned into NdeI/BamHI sites of pET28a(+) |
| pET28a(+)::gyh_cpl-1CBD | GyH ($PlyCA_{1-205}$) and Cpl-1 $CBD_{(191-339)}$, amplified using pET28a(+)::clyX-1 as template, cloned into NdeI/BamHI sites of pET28a(+) |
| pET28a(+)::plyCA_cpl-1 CBD | PlyCA and Cpl-1 $CBD_{(191-339)}$, fused via 1 round of SOE PCR cloned into NdeI/BamHI sites of pET28a(+) |
| pET28a(+)::plySs2_GH25 | PlySs2 full length and Cpl-1 EAD ($Cpl-1_{1-190}$), fused via 1 round of SOE PCR cloned into NdeI/BamHI sites of pET28a(+) |

*E. coli* BL21 (DE3) cells containing the recombinant proteins were grown in LB broth with carbenicillin or kanamycin (50 μg/mL). The culture was 1:100 diluted into fresh sterile LB broth supplemented with carbenicillin or overnight at 4° C. The proteins were concentrated to the desired concentration and sterilized through the 0.2 μm filter before store at −80° C. for further analysis. For in vivo murine model, the endotoxin was removed.

In a bacteriolytic assay, bacterial culture (stationary phase) was harvested at 5,000 for 10 min at 4° C., washed twice and resuspended in PBS buffer, pH7.4. In a 96-well titration plate, the resuspended bacterial solution was mixed 1:1 (u/u) with endolysin to a final $OD_{600}$ between 0.8 to 1.0. In each run, PBS was included as a negative control. Spectrophotometric readings ($OD_{600}$) were taken every 15 s over 10 min on a spectrophotometer. $V_{max}$ was calculated as the slope of the linear portion and represented the endolysins activity. All experiments were conducted in triplicate to get the standard deviation.

The optimal biochemical conditions for ClyX-1 against stationary phase S. pneumoniae TIGR 4 were determined using the turbidity reduction assay described above. For temperature stability, ClyX-1 was incubated at indicated temperatures (4° C., 16° C., 25° C., 37° C., 45° C., 55° C., or 65° C.)/tsb for 30 min, recovered on ice for 5 min, and subjected to the spectrophotometric analysis. For optimal pH condition, pneumococci TIGR 4 were suspended in 40 mM boric acid/phosphoric acid (BP) buffer, pH 3-10, and were challenged against ClyX-1.

With regard to bactericidal assay, bacterial cells were diluted to 2× rich media to generate a final concentration of $5.0 \times 10^6$ CFU/ml. 100 µl of the diluted bacterial culture was added into a 96-well titration plate in triplicate and mixed with 100 µl of sterile-filtered enzymes. Plates were sealed and incubated at 37° C. for 5-60 min. After the incubation, bacterial cells were serially diluted in 10-fold increments into sterile PBS and plated on THY/TSB agar. Log killing was calculated as follows: −log[(CFU under enzyme treatment)/(CFU under PBS treatment)].

The dimerization of ClyX-1 was based on the size change in the presence of choline monitored by the analytical gel filtration on a superose 12 column. Briefly, 500 µl of 1 mg/ml of ClyX-1 was injected in the sample loop. PBS and PBS with 50 mM choline were used as the elution buffer separately to determine the change of protein size. The standard protein size curve was obtained through the gel filtration standards.

The MICs of enzymes and antibiotics were determined in a 96-well titration plate in triplicate. Briefly, the overnight pneumococcal culture was diluted with 2×THY to obtain a final concentration of $1 \times 10^7$ CFU/ml, and other bacterial species were diluted with 2-folded medium to $1 \times 10^5$ CFU/ml. 100 µl of the diluted bacterial culture was subjected into each well, mixing with the serial 2-fold diluted 100 µl of enzymes/antibiotics. PBS buffer was used as a negative control. The plates were sealed via parafilm and statically incubated at 37° C. incubator for 24 h. The MIC was defined as the lowest concentration of treatment that inhibited visible growth of the bacterium.

The purification of the S. pyogenes D471 peptidoglycan was performed, wherein bacterial culture was pelleted at 5,000 rpm for 15 min in a centrifuge and resuspended in 25 ml of PBS per liter of cells. French Press using a cellular pressure of 15,000 p.s.i was applied twice to lyse the cells. The unbroken cells were removed at 5,000 rpm for 5 min. The supernatant was again subjected to centrifugation at 20,000 rpm for 45 min at 4° C. to pellet cell walls. The pelleted cell walls were rinsed and resuspended in PBS buffer supplemented with 0.2% (wt/vol) benzonase and proteinase K for 7 h. After incubation, the samples were boiled at 100° C. in 4% (wt/vol) SDS for 30 min, washed at least 3 times and resuspended in MiliQ water.

50 µg of PlyC in PBS buffer, pH 7.4, was added to S. pyogenes D471 cell wall suspensions ($OD_{600}=1.0$, PBS buffer, pH 7.4) respectively in a final volume of 500 µl. After digestion at 37° C. for 16 h, the reaction mixture was clarified by centrifugation (13,000 rpm, 5 min), and the supernatant was ultra filtered using a 5000-MW cutoff Vivaspin. The flow-through was aliquoted and prepared for the following mass spectrometry analysis.

With regard to in vivo mouse infection models, mouse infection experiments were carried out in an ABSL-2 lab. In the mouse systemic infection model, female BALB/c mice (6-8 weeks old) were injected intraperitoneally with S. pneumoniae NS26 at a single dose of $2.95 \times 10^7$ CFU/mouse and divided randomly into multiple groups. Bacterial burden in blood and organs in mice 1 h post-infected were confirmed by plating on THY agar as described previously. One hour post-infection, these groups intraperitoneally received a single dose of 20, 40, or 80 µg/mouse of PlyCpl-1 (n=10); 20, 40, or 80 µg/mouse of Cpl-1 (n=10); 100 µg/mouse of penicillin G (n=10); or an equal volume of PBS buffer (n=10). The survival data for all groups were recorded for 10 days.

With regard to host chimeras containing PlyCA, creating endolysins possessing highly active PlyCA against non-PlyC sensitive species started with shuffling with a specific binding CBD. Thus, Cpl-1 CBD which is dependent on the presence of choline residues in teichoic acid of pneumococcal strains was chosen as the bacterial recognition domain. FIG. 4 displays a schematic representation of the three engineered chimeric proteins (PlyCA_Cpl-1 CBD, ClyX-1, ClyX-1 linkers) and their parental proteins (PlyCA and Cpl-1).

PlyCA_Cpl-1 CBD contains full length of PlyCA at the N' termini and the full length of Cpl-1 CBD at the C' termini. The structure follows the typical native endolysins and the chimeric endolysins module, which is N' terminal EADs and C' terminal CBDs. ClyX-1 contains the full-length Cpl-1 CBD in the middle of the PlyCA to substitute the docking domain which does not affect activity, and ClyX-1-linkers is similar to ClyX-1 but with two extra native linkers in the PlyCA. Cloning, overproduction, and purification of the new enzymes were carried out. ClyX-1 and ClyX-1 linkers expressed as soluble enzymes and were purified to homogeneity based on SDS-PAGE analysis.

Figure 9:
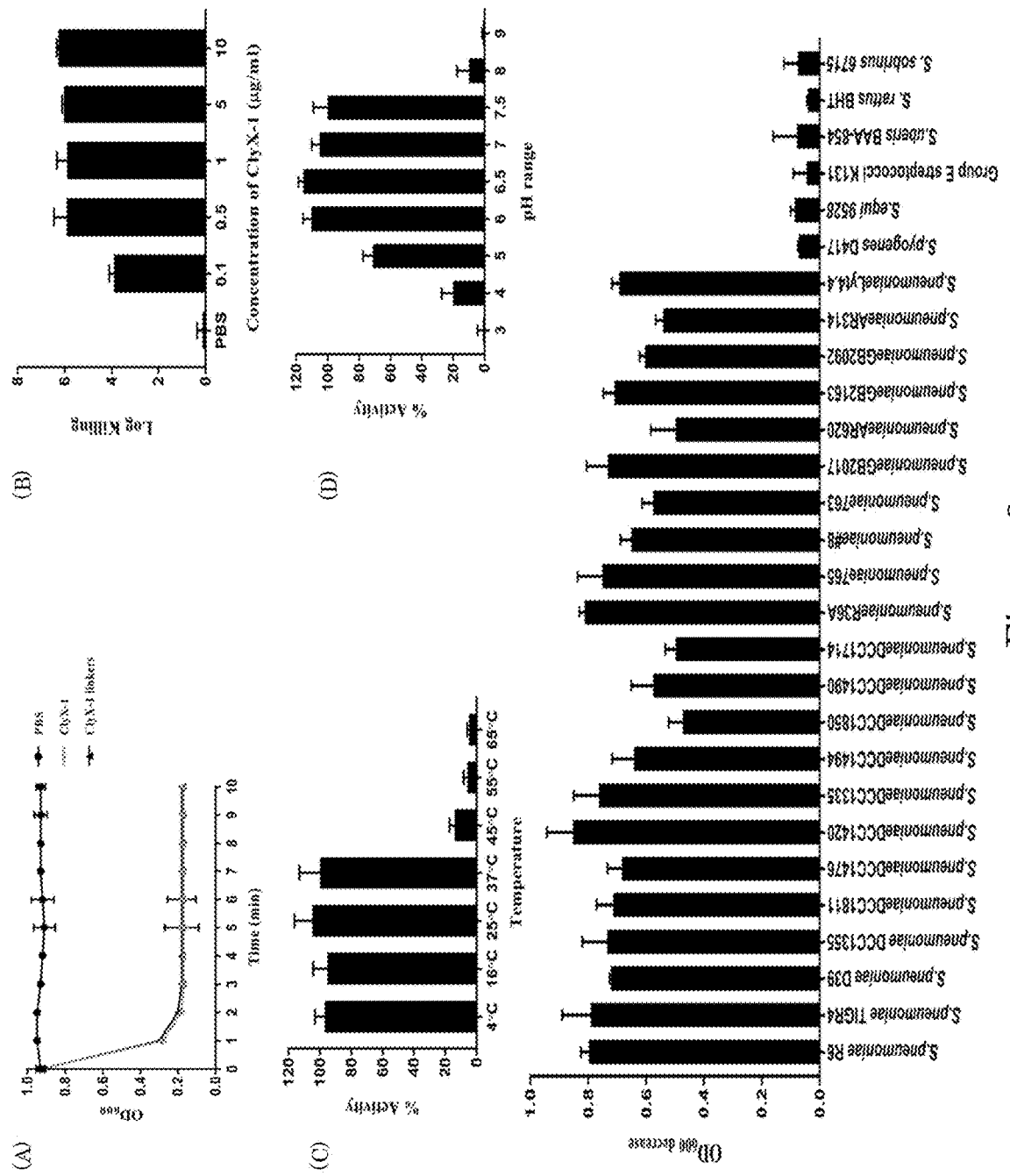
FIG. 9 shows (a) bacteriolytic effects of 5 µl/ml ClyX-1 and ClyX-1 linkers against stationary phase *Streptococcus pneumoniae* TIGR 4. (b) Bactericidal effects of ClyX-1 against stationary phase *S. pneumoniae* R6. Different concentrations of ClyX-1 were mixed with $10^6$ overnight bacterial culture for 5 min. Log killing was determined through the comparisons of PBS treatment and ClyX-1 treatment. (c)-(d) Biochemical characterization of ClyX-1. The effects of temperature stability (c) and pH (d) were evaluated. 5 µl/ml of ClyX-1 was assayed for lytic activity via turbidity reduction assay against stationary phase *S. pneumoniae* TIGR 4 cells for 10 min. Values were presented as percentage of lytic activity in a relation to activity observed for pH 7 and 37° C. (e) The host range of ClyX-1. Multiple strains of streptococci were tested for susceptibility. The bacterial cells were washed twice and resuspended in PBS to a final $OD_{600}$ of 0.9-1.0. The changes of $OD_{600}$ were presented after treating with 5 µl/ml of ClyX-1 for 10 min.

Bacteriolytic capacity of ClyX-1 and ClyX-1 linkers were analyzed via the turbidity reduction assay against the overnight culture of S. pneumoniae ATCC TIGR 4. Both enzymes-induced lysis of the bacterial peptidoglycan caused a decrease in OD from 1.0 to 0.2 (80%) within the first 2 min of the turbidity assay at 5 µg/ml as shown in FIG. 9a. The linkers were the only difference between these two enzymes, and the unstructured region of PlyCA GyH, PlyCA CHAP, and Cpl-1 CBD provide optimal flexibility for enzymatical activity. High lytic activity correlated with data for bacterial survival after chimera treatment. ClyX-1 sterilized cultures for 5 min, causing a decrease in TIGR 4 viability of ~6 log, at as low as 0.5 µg/ml (FIG. 9b). Stability of ClyX-1 at different temperature and pH was surveyed to determine optimal conditions. The ClyX-1 was stable below 37° C. to display the highest activity, but the activity rapidly dropped above 45° C. (FIG. 9). The Tm value of Cpl-1 CBD is 42.9° C., and the Tm value of PlyCA is 46.2° C. Loss of activity of ClyX-1 above 45° C. can be due to heat denaturation of the protein. The optimal pH condition is at pH 6.5 and lost at pH values above 8 and below 4 due to protein precipitation (FIG. 9d).

The antimicrobial spectrum of ClyX-1 was tested in vitro via turbidity reduction assay on a variety of S. pneumoniae strains and other streptococci. All tested strains of pneumococci were susceptible to ClyX-1 including the 14 most frequent serotypes, mutants that have a non-functional LytA (Lyt 4.4), and no capsule strains derived from D39 (R36A and R6) (FIG. 9e). The difference of OD decrease in different serotypes may be due to the accessibility of the peptidoglycan. The killing was specific for pneumococci, and there was lysis of no other streptococci tested. Collectively, our data suggest Cpl-1 CBD provides the specificity of ClyX-1 and retain the host range to pneumococci.

Figure 8:
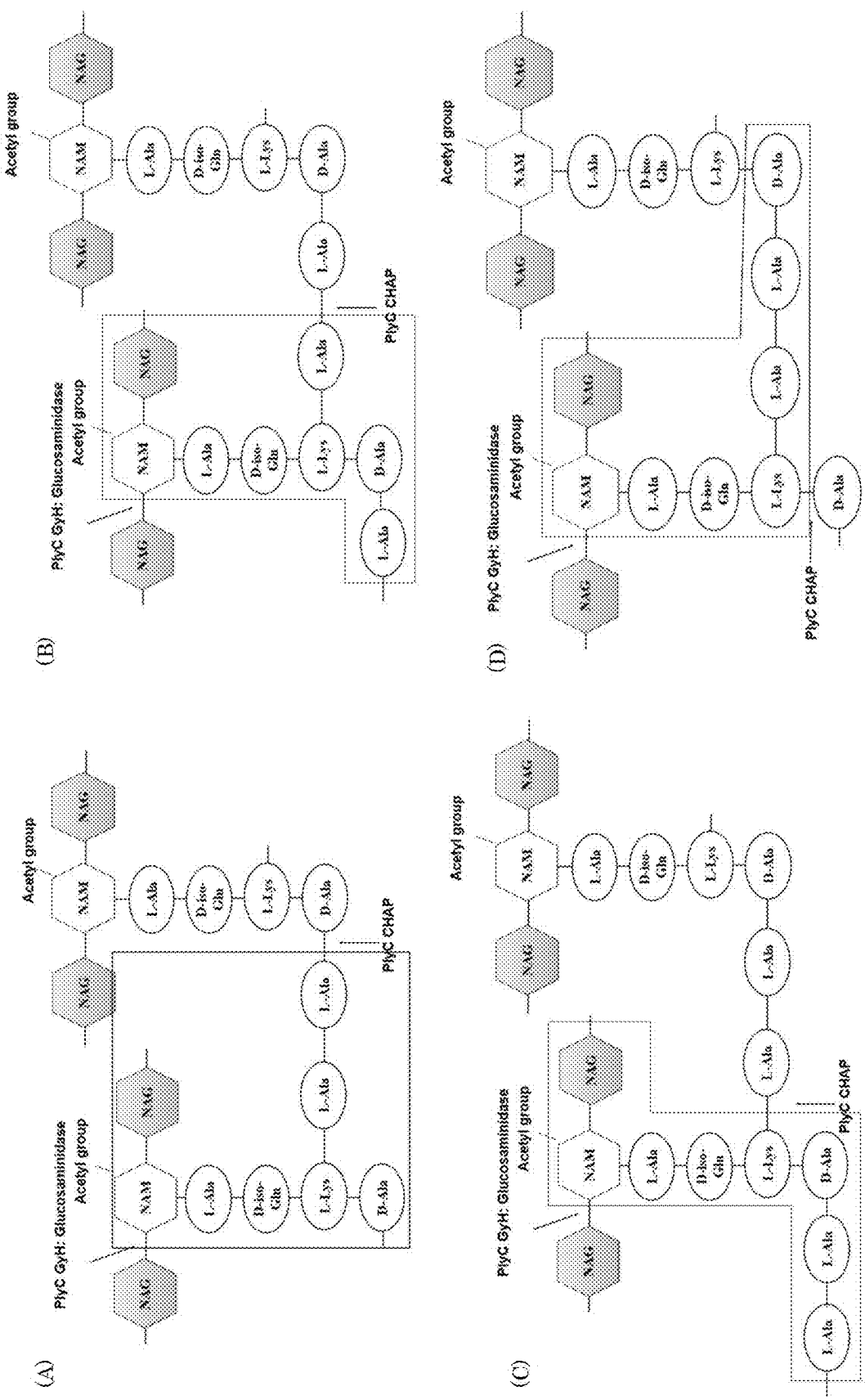
FIG. 8 shows structures for a muropeptide of peptidoglycan digested by PlyC.

We wondered if that Cpl-1 CBD still binds choline to form a dimer in the middle of two EADs. We used a simple analytical column via FLPC to monitor the change of the protein size in the presence of Choline. With 50 mM of choline in the PBS buffer, the curve shifted from ~57 kDa to ~114 kDa indicating that Cpl-1 CBD bound to choline and ClyX-1 formed a dimer (FIG. 8).

Figure 10:
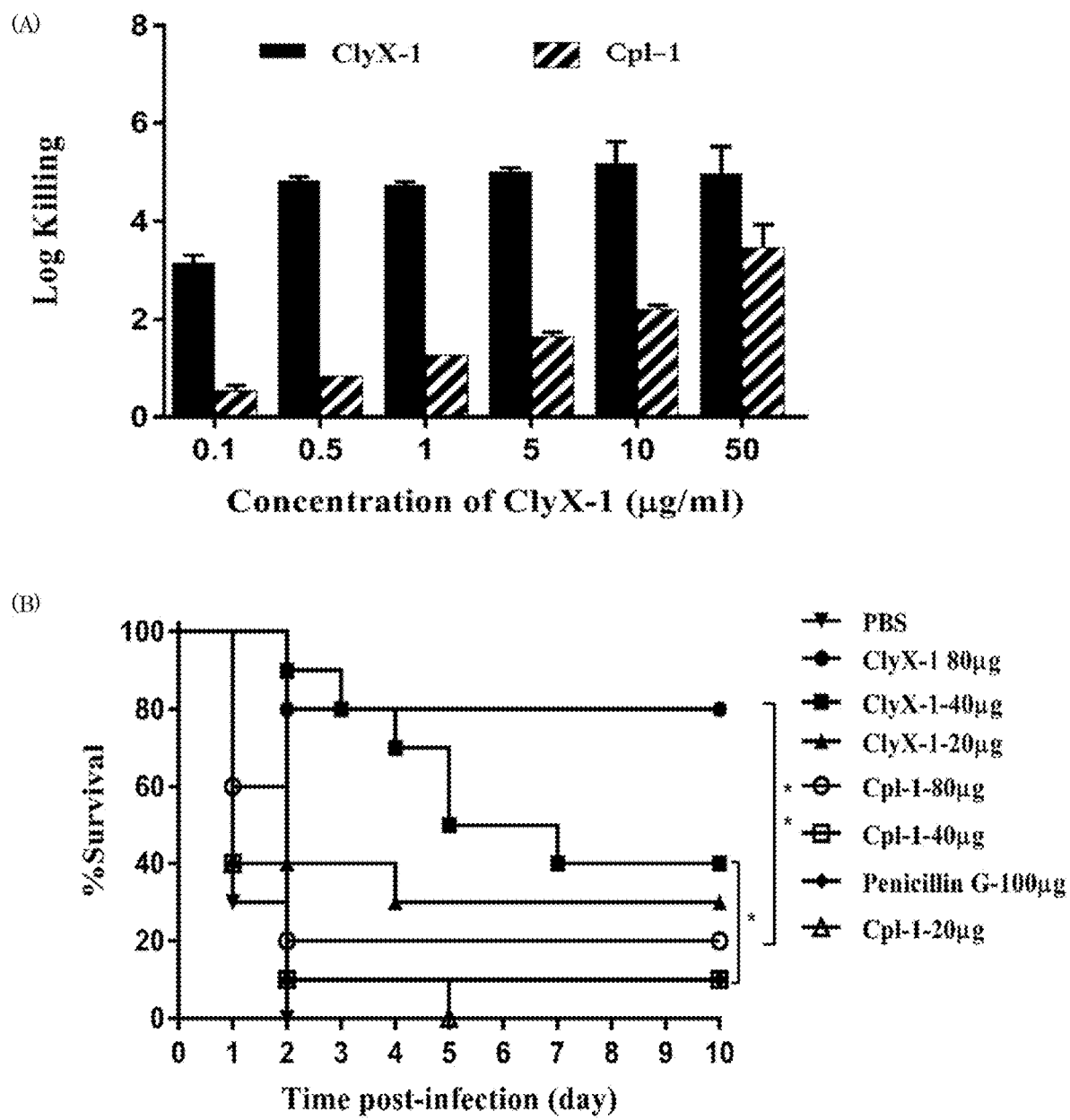
FIG. 10 shows comparisons of bactericidal activity of ClyX-1 and Cpl-1 in vitro and in vivo. (a) Different concentrations of ClyX-1 and Cpl-1 were mixed with $10^6$ overnight *S. pneumoniae* D39 culture for 5 min. The cells were then serial diluted and plated on the THY plates. Log killing was determined through the comparisons of PBS treatment and the enzymes treatment. (b) Female BALB/c mice were injected intraperitoneally with pneumococcus strain *S. pneumoniae* NS26 at a single dose at $2.95 \times 10^7$ colony forming units (CFU) per mouse. One hour after the infection, mice were intraperitoneally received a single dose of different treatments in different amount per mouse. The lines represent the percentage survival of mice for 10 days. The data was plotted as Kaplan-Meier survival curves and analyzed via the Log-rank (Mantel-Cox) test (*P<0.001; **P<0.0001)

ClyX-1 is more active than parental enzymes in vitro and in vivo. After demonstrating the extremely high activity of ClyX-1, we compared its efficacy with Cpl-1 in vitro and in vivo. Bactericidal assays were repeated using the three lysins at different concentrations (0.5 µg/ml to 50 µg/ml) on a different strain, D39 (FIG. 10a). ClyX-1 sterilized the bacteria culture within 5 min at even the lowest concentration (0.5 µg/ml), while Cpl-1 also sterilized the culture but at the 50 µg/ml and only reduced <1 log at 0.5 µg/ml. PlyCA displayed no bactericidal activity against pneumococci, wherein PlyCA has no lytic activity in the absence of PlyC CBD (PlyCB). Full-length of PlyC (with PlyCB as the CBD) may not be lytic to pneumococci due to limitation of PlyCB.

Figure 13:
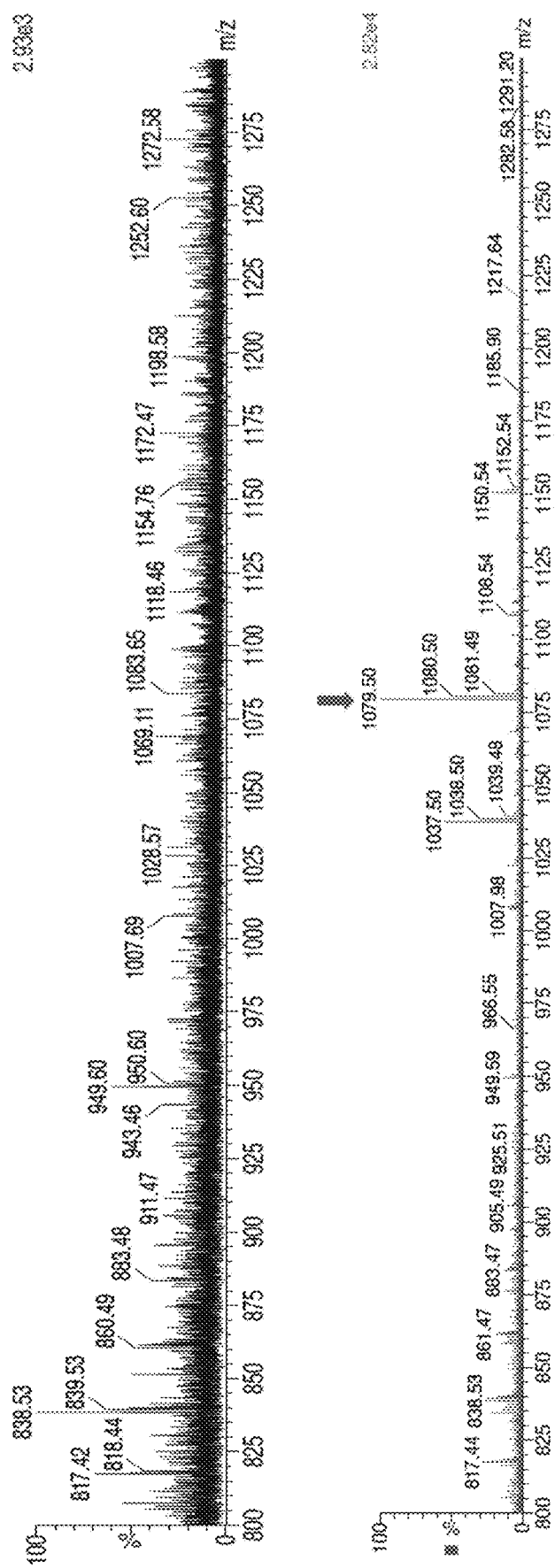
FIG. 13 shows cleavage specificity of PlyCA GyH and PlyCA CHAP. (a) MS analysis of undigested peptidoglycan (top) and PlyC-digested peptidoglycan (bottom). (b) MS analysis of undigested AQKAAAK peptide and PlyCΔGyH-digested AQKAAAK peptide. (c) Schematic showing the PlyCA GyH and CHAP cleaved fragment.

To further evaluate the activity of ClyX-1, MIC tests were performed against eight serotypes of pneumococci including penicillin-resistant strains and capsule-free mutant with information shown in FIG. 13. Penicillin and levofloxacin were tested as standards to benchmark the antimicrobial activity. All of the strains were sensitive to levofloxacin (MIC<=2). Only the two penicillin-resistant strains indicated MIC larger than 2 µg/ml (resistance). The Cpl-1 MIC for all strains was between 16 µg/ml-32 µg/ml. The MICs of ClyX-1 were lower than that of Cpl-1 and even levofloxacin, ranging from 0.13 µg/ml to 0.5 µg/ml. For the two penicillin-resistant strains, ClyX-1 displayed much lower MIC.

To validate the in vitro bactericidal activity of ClyX-1, we applied a mouse systemic infection model to test the in vivo efficacy of the enzyme. Mice were challenged to a 2-days lethal-dose of $2.95 \times 10^7$ CFU. One hour after infection, the mice were intraperitoneally injected a single dose containing different amount of either ClyX-1 or Cpl-1 ranging from 20 µg-80 µg. The antibiotics control was 100 µg/mouse of penicillin G, and the negative control was as PBS, pH7.4 buffer. The mice were then observed and recorded for the survival data. All the mice treated with PBS buffer died within the first 2 days. ClyX-1 treatment resulted in rescuing 80%, 40% and 30% of the mice responding to the dose of 80 µg, 40 µg, and 20 g. The highest amount of Cpl-1, 80 µg, resulted in rescuing 20%, and the mice treated with 20 µg of Cpl-1 had died within the first 5 days (FIG. 10b). These observations suggest that ClyX-1 is much more active than Cpl-1 in vitro and in vivo.

Figure 11:
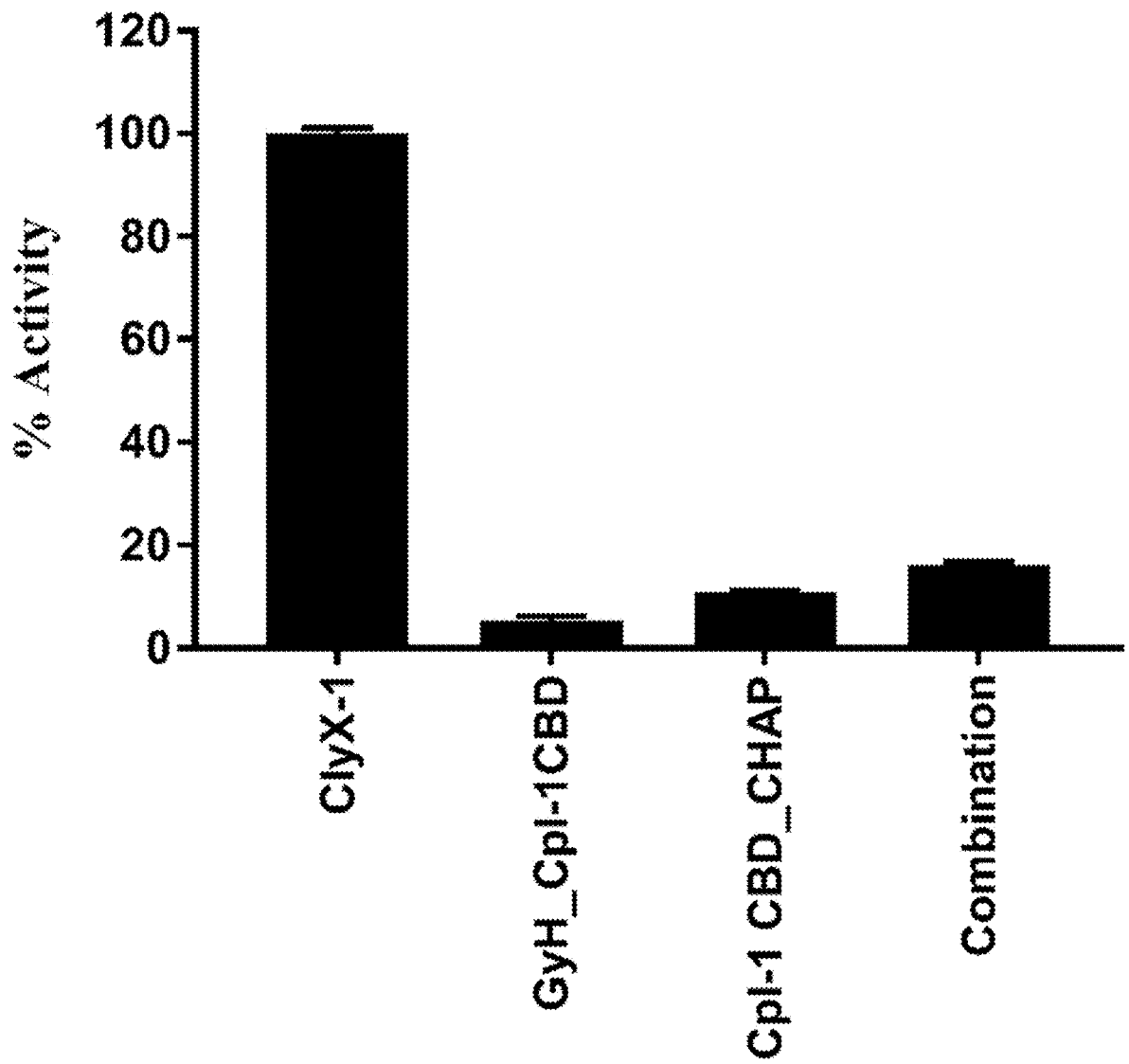
FIG. 11 shows synergy among GyH and CHAP domains in ClyX-1. The constructs of GyH_Cpl-1 CBD(ClyX-$1_{1-356}$) and Cpl-1 CBD_CHAP(ClyX-$1_{205-512}$) were cloned and expressed for the synergy test. 5 µl/ml of each enzyme was used for the lytic activity via turbidity reduction assay against stationary phase *S. pneumoniae* R6 cells for 10 min. For the combination group, 2.5 µl/ml of GyH_Cpl-1 CBD (ClyX-$1_{1-356}$) and Cpl-1 CBD_CHAP(ClyX-$1_{205-512}$) were used. Values are presented as percentage of lytic activity in relation to highest activity observed.

The high activity of ClyX-1 is due to the synergistic effects of both catalytic domains. To confirm the synergy of GyH and CHAP domains in ClyX-1, we examined the activity of each domain separately. First, we made the constructs of GyH_Cpl-1 CBD (ClyX-$1_{1-356}$) and Cpl-1 CBD_CHAP (ClyX-$1_{205-512}$), each of which consists of Cpl-1 CBD and functional EAD from ClyX-1. Then, we analyzed the lytic activity via turbidity reduction assay and MICs of ClyX-1, GyH_Cpl-1 CBD (ClyX-$1_{1-356}$), Cpl-1 CBD_CHAP (ClyX-$1_{205-512}$), and the combination of the constructs. Both constructs only displayed less than 20% activity of ClyX-1, and the combination in a 1:1 amount ratio did not restore the ClyX-1 lytic activity (FIG. 11). The MICs' evaluation was consistent with the lytic activity (FIG. 13). Both constructs had ~64-100-folded MICs of ClyX-1, and in the combination treatment, the MICs were still ~64-100 times higher. GyH and CHAP domains in ClyX-1 elucidate synergistic effects due to the positioning of catalytic domains in ClyX-1.

Figure 12:
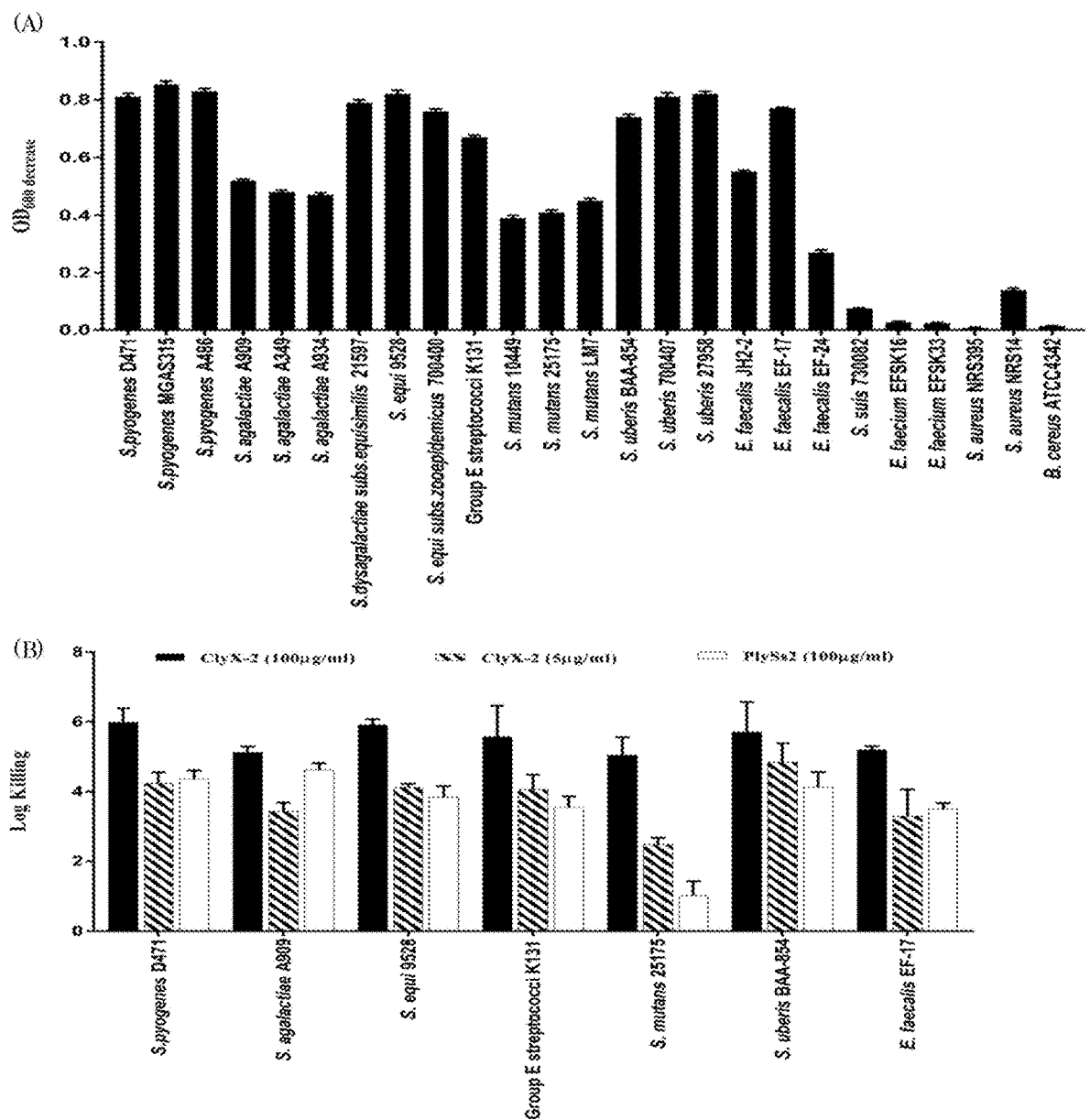
FIG. 12 shows a lytic profile and bactericidal activity of ClyX-2. (a) Host range of ClyX-2. Different bacterial strains were used to test susceptibility via turbidity reduction assay. The values were presented as the decrease of $OD_{600}$ in 10 min with 25 µg/ml of ClyX-2. (b) Bactericidal activity of ClyX-2. PlySs2 and ClyX-2 were mixed with $10^6$ bacterial culture for 1 h. Log killing was determined by comparisons of PBS treatment and ClyX-1 treatment.

With regard to design and engineer a broad host range chimera containing PlyCA, a CBD was disposed in the middle of the GyH and CHAP to display the synergy. We selected a broad host range CBD belonging to the SH3-5 family of PlySs2. The PlySs2 CBD was engineered in the middle of GyH and CHAP in the same way as ClyX-1, and we named it ClyX-2 (FIG. 4). The host spectrum was analyzed via the turbidity reduction assay. ClyX-2 retained the host range of PlyC (GAS, GCS, GES and S. uberis) but also expanded to GBS, S. mutans and E. faecalis, which was due to the binding activity of PlySs2 CBD (FIG. 12a). The bactericidal efficacy of ClyX-2 and PlySs2 was first compared via log killing (FIG. 12b). On all bacteria tested, 10 µg of ClyX-2 caused a ~6 log reduction in CFU while the same amount of PlySs2 caused a ~4 log reduction. Decreasing the amount of ClyX-2 to 0.5 µg resulted in the similar log reduction as that of PlySs2 at 10 µg. In a similar manner, the MICs of ClyX-2 were lower than that of PlySs2, especially for GAS (2 µg/ml v.s. 128 µg/ml) and GCS (4 µg/ml v.s.>512 µg/ml) (FIG. 16). These results strengthen the idea that the CBD can be engineered in the middle of GyH and CHAP as well as retaining the CBD's host range and exploiting the synergy of these two catalytic domains.

With regard to determining cleavage specificity of PlyCA GyH and PlyCA CHAP, to figure the specific cleavage sites, PlyC digested S. pyogenes D471 peptidoglycan was analyzed via mass spectrometry (MS). Surprisingly, a muropeptide with the m/z value of 1079.5 corresponding to the size of O-acetylated N-acetylmuramic acid (NAM) and N-acetyl-glucosamine (NAG) with $A_4QK$ (FIG. 13a) was the most abundant species after digestion, wherein CHAP was not amidase cleaving between NAM and L-alanine of the stem peptide. Moreover, PlyC GyH was a glucosaminidase due to the cleavage of the O-acetylated NAM, but left four possible cutting sites of PlyC CHAP (FIG. 8). A synthesized peptide (AQKAAAK) was then used to assess the cutting site of PlyC CHAP.

Figure 6:
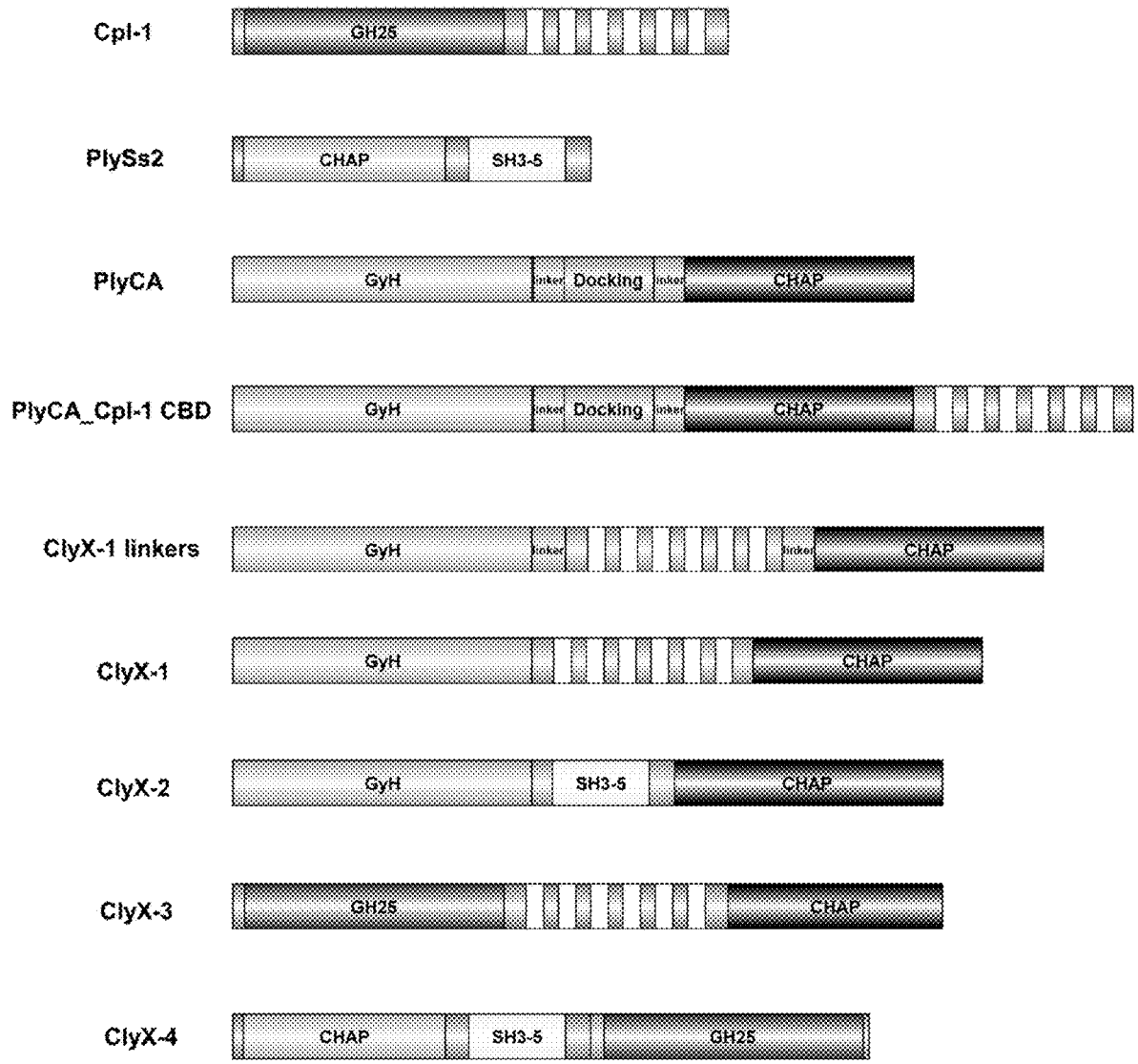
FIG. 6 shows a plurality of constructs.
Figure 7:
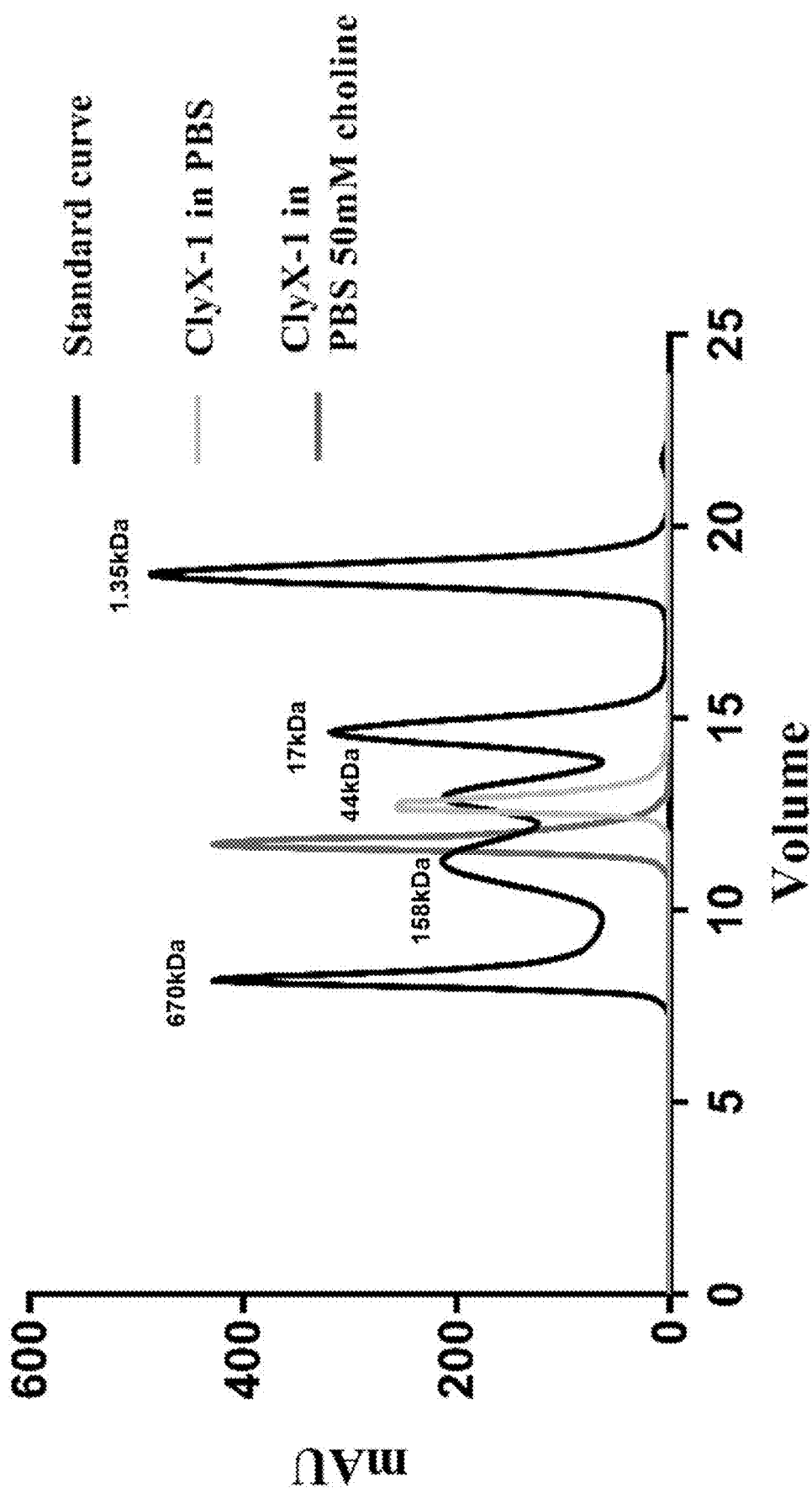
FIG. 7 shows a graph of molecular size based on gel filtration.
Figure 14:
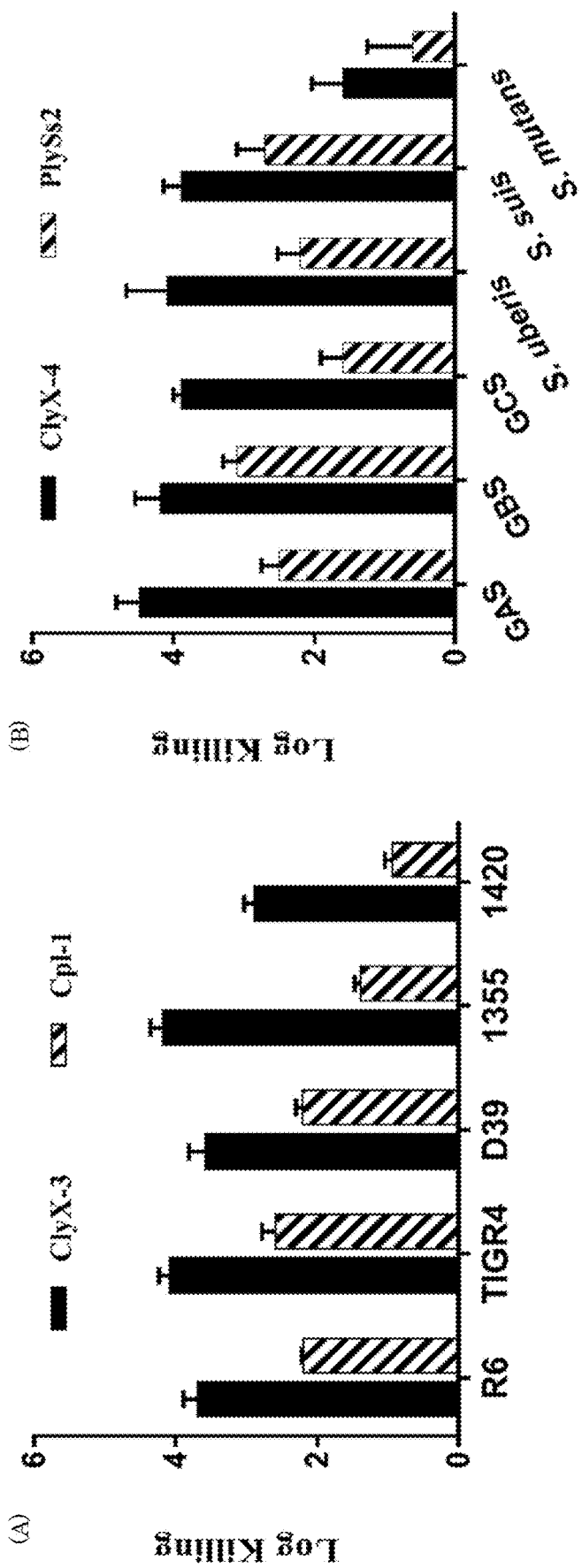
FIG. 14 shows bactericidal activity of ClyX-3 and ClyX-4. (a) Bactericidal effects of ClyX-3 against five strains of stationary phase *S. pneumoniae*. 5 µg/ml of enzymes were mixed with $10^6$ bacterial cultures for 5 min. Log killing was determined through the comparisons of PBS treatment and enzymes treatment. (b) Bactericidal effects of ClyX-4 against stationary phase streptococci. 50 µg/ml of enzymes were mixed with $10^6$ bacterial culture for 1 h. Log killing was determined through the comparisons of PBS treatment and enzymes treatment.

With regard to applying the design rationale to add a C' terminal EAD such that two EADs are disposed at each side of the CBD, the process was used to engineer endolysins for increased activity. We created the ClyX-3, the full-length Cpl-1 with an additional C' terminal PlyC CHAP, and ClyX-4, the full-length PlySs2 with an additional C' terminal Cpl-1 EAD (GH25) (FIG. 4 and FIG. 6). These constructs were expressed and purified as soluble proteins. We found that ClyX-3 was capable of reducing ~4 logs of the tested pneumococcal strains, whereas Cpl-1 only caused ~2 logs reduction (FIG. 14a). Similarly, the ClyX-4 was more active than PlySs2 against GAS, GBS, GCS, S. uberis, S. suis and S. mutants (FIG. 14b). These results conclude that the additional C' terminal EAD can function normally to cleave the peptidoglycan with the proper space provided by the CBD. Via further analysis of the MICs, we noticed that although the activity of ClyX-3 and ClyX-4 were better than parental endolysins, they were still less active compared to ClyX-1 and ClyX-2 possessing the synergy activity (FIG. 15 and FIG. 16). These observations suggest that the two EADs in ClyX-3 and ClyX-4 may display synergistic effect, but not to the same extent as that of PlyC GyH and CHAP domains.

With regard to synergy of PlyC GyH and CHAP domains, our novel design includes the CBD in the middle of two EADs that provided chimeric endolysins, ClyX-1 and ClyX-2, with high activity and demonstrated a method for engineering endolysins.

Although PlyC has the multimeric structure, it is not the only endolysin harboring two catalytic domains. As the discovery of the new endolysins, the structures of them are not necessarily limited to two modules. Numerous endolysins have been proved to possess two short lytic domains. Several examples of dual catalytic domains are: *Staphylococcus* phage K endolysin, LysK, contains both CHAP endopeptidases at N' terminal and an amidase domain in the middle; the GBS lysin B30 has both N-acetylmuramidase and D-alanyl-L-alanyl endopeptidase at the N' terminal; the streptococcal λsa2 phage endolysin consists of the centrally located CBD separating N' terminal D-glutaminyl-L-lysin endopeptidase and C' terminal N-acetylglucosaminidase. Nevertheless, the second catalytic domains in these endolysins are silent in enzymatical activity responsible for bacterial cell lysis from without. Toward this end, PlyC is the unique endolysin that harness synergistically enzymatical activity of PlyCA GyH and CHAP domains.

Triple-acting chimeric endolysins can include three cleavage domains. Even though the triple-lytic-domain lysins performed better to prevent the resistant strain development, the lysins did not arm better activity with three catalytic domains compared to one catalytic domain. Synergistic catalytic domains, PlyC GyH and CHAP, are a start point for engineering highly active endolysins. Due to the success of the domain swapping method, we added a CBD to C' terminal of PlyCA, but none of the constructs are expressed. We decided to replace the docking domain, linking GyH and CHAP, with a CBD. ClyX-1 and ClyX-1 linkers displayed similar activity, wherein linkers in PlyCA were not necessary for the synergistic effect. ClyX-1 still retained the host range as that of the CBD via the choline binding domain. The analytical gel filtration data elucidated that the CBD of ClyX-1 formed a dimer in the presence of choline, wherein the central position of Cpl-1 CBD did not influence protein folding and conformational change during binding. The broad host spectrum CBD, SH3-5 of PlySs2, folded and functioned in center of PlyC GyH and CHAP. Furthermore, ClyX-1 and ClyX-2 harnessed the synergy of two catalytic domains displaying improved bactericidal activity both in vitro and in vivo.

Through ClyX-1 and ClyX-2, central CBD provided binding specificity and space for two EADs reaching and cutting substrates. EADs, Cpl-1 EAD (GH25) and PlyC CHAP, did not show a synergistic or additive effect when mixed. However, being cloned in one endolysin as ClyX-3, they displayed synergistic activity leading to increased enzymatic activity. ClyX-4 performed similarly that by cloning the two EADs, PlySs2 CHAP and Cpl-2 EAD (GH25) as one endolysin, they displayed increased activity. Activity of ClyX-3 and ClyX-4 were less than that of ClyX-1 and ClyX-2 since the GyH and CHAP together show potent activity. CBD in the middle of two EADs is a method to engineer endolysins.

The process for making the di-enzymatic chimeric endolysins described in this Example, harness potent efficacy of PlyC towards streptococcal species. Via bacteriolytic and bactericidal tests in vitro and in vivo, we confirmed that ClyX-1 and ClyX-2 displayed dramatically improved activity due to the synergy from GyH and CHAP domains. By applying the idea to design two EADs endolysins, we created ClyX-3 and ClyX-4 in which the two EADs functioned by proper space provided by the CBD and displayed synergistic effects. Finally, the novel design can be subjected to engineer double-acting endolysins.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A di-enzymatic chimeric endolysin comprising:

a primary enzymatic active domain disposed at an N-terminus end of the di-enzymatic chimeric endolysin, the primary enzymatic active domain comprising a primary protein sequence and that cleaves a glycosidic bond, a peptide bond, or an amide bond of a peptidoglycan in a cell wall of a cell;

a secondary enzymatic active domain disposed at a C-terminus end of the di-enzymatic chimeric endolysin, the secondary enzymatic active domain comprising a secondary protein sequence and that, in combination with the primary enzymatic active domain, synergistically cleaves glycosidic bonds, peptide bonds, or amide bonds in the peptidoglycan in the cell wall;

a cell wall binding domain:
comprising a recognition sequence;
chemically attached to the primary protein sequence and the secondary protein sequence,
sequentially interposed between the primary protein sequence and the secondary protein sequence, and
that binds to a cell wall; and a tertiary structure formed by folding of the primary protein sequence and the secondary protein sequence such that the primary enzymatic active domain faces and opposes the secondary enzymatic active domain in the di-enzymatic chimeric endolysin for synergistic cleavage of the peptidoglycan in the cell wall.

2. The di-enzymatic chimeric endolysin of claim 1, further comprising a first linker interposed between the primary protein sequence and the recognition sequence.

3. The di-enzymatic chimeric endolysin of claim 2, wherein the first linker comprises:

```
                                    (Sequence ID No. 4)
TGDGKNPSVGTGNATVSASSE
or
                                    (Sequence ID No. 5)
TGDGKNPSVGTGNATVSASSECT.
```

4. The di-enzymatic chimeric endolysin of claim 1, further comprising a second linker interposed between the secondary protein sequence and the recognition sequence.

5. The di-enzymatic chimeric endolysin of claim 4, wherein the second linker comprises

```
                                    (Sequence ID No. 6)
QTNPNPDKPTVKSPGQNDLGS
or
                                    (Sequence ID No. 7)
LQQTNPNPDKPTVKSPGQNDLGS.
```

6. The di-enzymatic chimeric endolysin of claim 1, wherein the primary protein sequence comprises

```
                                    (Sequence ID No. 1)
MSKKYTQQQYEKYLAQPANNTFGLSPQQVADWFMGQAGARPVINSYGVNAS

NLVSTYIPKMQEYGVSYTLFLMYTVFEGGGAGNWINHYMYDTGSNGLECLE

HDLQYIHGVWETYFPPALSAPECYPATEDNAGALDRFYQSLPGRTWGDVMI

PSTMAGNAWVWAYNYCVNNQGAAPLVYFGNPYDSQIDSLLAMGADPFTGGS

I, (Sequence ID No. 2)
MVKKNDLFVDVSSHNGYDITGILEQMGTTNTIIKISESTTYLNPCLSAQVE

QSNPIGFYHFARFGGDVAEAEREAQFFLDNVPMQVKYLVLDYEDDPSGDAQ

ANTNACLRFMQMIADAGYKPIYYSYKPFTHDNVDYQQILAQFPNSLWIAGY

GLNDGTANFEYFPSMDGIRWWQYSSNPFDKNIVLLDD,
or
                                    (Sequence ID No. 3)
MTTVNEALNNVRAQVGSGVSVGNGECYALASWYERMISPDATVGLGAGVGW

VSGAIGDTISAKNIGSSYNWQANGWTVSTSGPFKAGQIVTLGATPGNPYGH

VVIVEAVDGDRLTILEQNYGGKRYPVRNYYSAASYRQQVVHYIT.
```

7. The di-enzymatic chimeric endolysin of claim 1, wherein the secondary protein sequence comprises

```
                                    (Sequence ID No. 8)
GSDRVAANLANAQAQVGKYIGDGQCYAWVGWWSARVCGYSISYSTGDPMLP

LIGDGMNAHSIHLGWDWSIANTGIVNYPVGTVGRKEDLRVGAIWCATAFSG

APFYTGQYGHTGIIESWSDTTVTVLEQNILGSPVIRSTYDLNTFLSTLTGL

ITFK
or
                                    (Sequence ID No. 9)
MVKKNDLFVDVSSHNGYDITGILEQMGTTNTIIKISESTTYLNPCLSAQVE

QSNPIGFYHFARFGGDVAEAEREAQFFLDNVPMQVKYLVLDYEDDPSGDAQ

ANTNACLRFMQMIADAGYKPIYYSYKPFTHDNVDYQQILAQFPNSLWIAGY

GLNDGTANFEYFPSMDGIRWWQYSSNPFDKNIVLLDDEEDDKPKTAGTWKQ

DSKGWWFRRNNGSFPY.
```

8. The di-enzymatic chimeric endolysin of claim 1, wherein the recognition sequence comprises

```
                                    (Sequence ID No. 10)
ANREKLKKALTDLFNNNLEHLSGEFYGNQVLNAMKYGTILKCDLTDDGLNA

ILQLIADVNL, (Sequence ID No. 11)
MEEDDKPKTAGTWKQDSKGWWFRRNNGSFPYNKWEKIGGVWYYFDSKGYCL

TSEWLKDNEKWYYLKDNGAMATGWVLVGSEWYYMDDSGAMVTGWVKYKNNW

YYMTNERGNMVSNEFIKSGKGWYFMNTNGELADNPSFTKEPDGLITVA, (Sequence ID No. 12)
EEDDKPKTAGTWKQDSKGWWFRRNNGSFPYNKWEKIGGVWYYFDSKGYCLT

SEWLKDNEKWYYLKDNGAMATGWVLVGSEWYYMDDSGAMVTGWVKYKNNWY

YMTNERGNMVSNEFIKSGKGWYFMNTNGELADNPSFTKEPDGLITVA,
or
                                    (Sequence ID No.13)
GTMPPGTVAQSAPNLAGSRSYRETGTMTVTVDALNVRRAPNTSGEIVAVYK

RGESFDYDTVIIDVNGYVWVSYIGGSGKRNYVATGATKDGKRFGNAWGTFK

TS, (Sequence ID No. 14)
MPPGTVAQSAPNLAGSRSYRETGTMTVTVDALNVRRAPNTSGEIVAVYKRG

ESFDYDTVIIDVNGYVWVSYIGGSGKRNYVATGATKDGKRFGNAWGTFK,
or
                                    (Sequence ID No. 15)
PPGTVAQSAPNLAGSRSYRETGTMTVTVDALNVRRAPNTSGEIVAVYKRGE

SFDYDTVIIDVNGYVWVSYIGGSGKRNYVATGATKDGKRFGNAWGTFK.
```

9. The di-enzymatic chimeric endolysin of claim 1, wherein the cell comprises a bacterial cell.

10. The di-enzymatic chimeric endolysin of claim 1, wherein the bacterial cell comprises a Gram-positive bacterium.

11. The di-enzymatic chimeric endolysin of claim 9, wherein the bacterial cell comprises a pneumococcus, *Staphylococcus*, *Streptococcus*, *Corynebacterium*, *Clostridium*, *Listeria*, *Bacillus*, *Cutibacterium*, *Lactococcus*, or a combination comprising at least one of the foregoing bacterial cells.

12. The di-enzymatic chimeric endolysin of claim 1, wherein the bacterial cell comprises a Gram-negative bacterium.

13. The di-enzymatic chimeric endolysin of claim 9, wherein the bacterial cell comprises *Escherichia*, *Salmonella*, *Shigella*, *Pseudomonas*, *Moraxella*, *Helicobacter*, *Stenotrophomonas*, *Bdellovibrio*, *Neisseria*, *Haemophilus*, *Klebsiella*, *Legionella*, *Pseudomonas*, *Proteus*, *Enterobacter*, *Serratia*, *Helicobacter*, or *Acinetobacter*, or a combination comprising at least one of the foregoing bacterial cells.

14. The di-enzymatic chimeric endolysin of claim 1, wherein the di-enzymatic chimeric endolysin is ClyX-1, ClyX-2, ClyX-3, or ClyX-4.

15. A process for lysing a cell with a di-enzymatic chimeric endolysin, the process comprising:
contacting a cell wall of the cell with the di-enzymatic chimeric endolysin, the di-enzymatic chimeric endolysin comprising:
  a primary enzymatic active domain disposed at an N-terminus end of the di-enzymatic chimeric endolysin, the primary enzymatic active domain comprising a primary protein sequence and that cleaves a glycosidic bond, a peptide bond, or an amide bond of a peptidoglycan in a cell wall of a cell;
  a secondary enzymatic active domain disposed at a C-terminus end of the di-enzymatic chimeric endolysin, the secondary enzymatic active domain comprising a secondary protein sequence and that, in combination with the primary enzymatic active domain, synergistically cleaves glycosidic bonds, peptide bonds, or amide bonds in the peptidoglycan in the cell wall;
  a cell wall binding domain:
    comprising a recognition sequence;
    chemically attached to the primary protein sequence and the secondary protein sequence,
    sequentially interposed between the primary protein sequence and the secondary protein sequence, and that binds to a cell wall; and
  a tertiary structure formed by folding of the primary protein sequence and the secondary protein sequence such that the primary enzymatic active domain faces and opposes the secondary enzymatic active domain in the di-enzymatic chimeric endolysin for synergistic cleavage of the peptidoglycan in the cell wall;
cleaving, by the primary enzymatic active domain, a first glycosidic bond, a peptide bond, or an amide bond of the peptidoglycan in the cell wall of the cell;
cleaving, by the secondary enzymatic active domain, a second glycosidic bond, peptide bond, or amide bond of the peptidoglycan in the cell wall of the cell; and
lysing the cell in response to cleaving the glycosidic bonds, peptide bonds, or amide bonds of the cell wall.

16. The process for lysing a cell of claim 15, wherein the di-enzymatic chimeric endolysin further comprises a first linker interposed between the primary protein sequence and the recognition sequence, the first linker comprising TGDGKNPSVGTGNATVSASSE (Sequence ID No. 4) or TGDGKNPSVGTGNATVSASSECT (Sequence ID No. 5).

17. The process for lysing a cell of claim 15, wherein the di-enzymatic chimeric endolysin further comprises a second linker interposed between the secondary protein sequence and the recognition sequence, the second linker comprising QTNPNPDKPTVKSPGQNDLGS (Sequence ID No. 6) or LQQTNPNPDKPTVKSPGQNDLGS (Sequence ID No. 7).

18. The process for lysing a cell of claim 15, wherein the primary protein sequence comprises (Sequence ID No. 1)
MSKKYTQQQYEKYLAQPANNTFGLSPQQVADWFMGQAGARPVINSYGVNAS

NLVSTYIPKMQEYGVSYTLFLMYTVFEGGGAGNWINHYMYDTGSNGLECLE

HDLQYIHGVWETYFPPALSAPECYPATEDNAGALDRFYQSLPGRTWGDVMI

PSTMAGNAWVWAYNYCVNNQGAAPLVYFGNPYDSQIDSLLAMGADPFTGGS

I, (Sequence ID No. 2)
MVKKNDLFVDVSSHNGYDITGILEQMGTTNTIIKISESTTYLNPCLSAQVE

QSNPIGFYHFARFGGDVAEAEREAQFFLDNVPMQVKYLVLDYEDDPSGDAQ

ANTNACLRFMQMIADAGYKPIYYSYKPFTHDNVDYQQILAQFPNSLWIAGY

GLNDGTANFEYFPSMDGIRWWQYSSNPFDKNIVLLDD,
or (Sequence ID No. 3)
MTTVNEALNNVRAQVGSGVSVGNGECYALASWYERMISPDATVGLGAGVGW

VSGAIGDTISAKNIGSSYNWQANGWTVSTSGPFKAGQIVTLGATPGNPYGH

VVIVEAVDGDRLTILEQNYGGKRYPVRNYYSAASYRQQVVHYIT.

19. The process for lysing a cell of claim 15, wherein the secondary protein sequence comprises (Sequence ID No. 8)
GSDRVAANLANAQAQVGKYIGDGQCYAWVGWWSARVCGYSISYSTGDPMLP

LIGDGMNAHSIHLGWDWSIANTGIVNYPVGTVGRKEDLRVGAIWCATAFSG

APFYTGQYGHTGIIESWSDTTVTVLEQNILGSPVIRSTYDLNTFLSTLTGL

ITFK
or (Sequence ID No. 9)
MVKKNDLFVDVSSHNGYDITGILEQMGTTNTIIKISESTTYLNPCLSAQVE

QSNPIGFYHFARFGGDVAEAEREAQFFLDNVPMQVKYLVLDYEDDPSGDAQ

ANTNACLRFMQMIADAGYKPIYYSYKPFTHDNVDYQQILAQFPNSLWIAGY

GLNDGTANFEYFPSMDGIRWWQYSSNPFDKNIVLLDDEEDDKPKTAGTWKQ

DSKGWWFRRNNGSFPY.

20. The process for lysing a cell of claim 15, wherein the recognition sequence comprises (Sequence ID No. 10)
ANREKLKKALTDLFNNNLEHLSGEFYGNQVLNAMKYGTILKCDLTDDGLNA

ILQLIADVNL, (Sequence ID No. 11)
MEEDDKPKTAGTWKQDSKGWWFRRNNGSFPYNKWEKIGGVWYYFDSKGYCL

TSEWLKDNEKWYYLKDNGAMATGWVLVGSEWYYMDDSGAMVTGWVKYKNNW

YYMTNERGNMVSNEFIKSGKGWYFMNTNGELADNPSFTKEPDGLITVA, (Sequence ID No. 12 )
EEDDKPKTAGTWKQDSKGWWFRRNNGSFPYNKWEKIGGVWYYFDSKGYCLT

SEWLKDNEKWYYLKDNGAMATGWVLVGSEWYYMDDSGAMVTGWVKYKNNWY

YMTNERGNMVSNEFIKSGKGWYFMNTNGELADNPSFTKEPDGLITVA,
or (Sequence ID No. 13)
GTMPPGTVAQSAPNLAGSRSYRETGTMTVTVDALNVRRAPNTSGEIVAVYK

RGESFDYDTVIIDVNGYVWVSYIGGSGKRNYVATGATKDGKRFGNAWGTFK

TS,
or (Sequence ID No. 14)
MPPGTVAQSAPNLAGSRSYRETGTMTVTVDALNVRRAPNTSGEIVAVYKRG

ESFDYDTVIIDVNGYVWVSYIGGSGKRNYVATGATKDGKRFGNAWGTFK,

-continued (Sequence ID No. 15)
PPGTVAQSAPNLAGSRSYRETGTMTVTVDALNVRRAPNTSGEIVAVYKRGE

SFDYDTVIIDVNGYVWVSYIGGSGKRNYVATGATKDGKRFGNAWGTFK.

* * * * *